US006856344B2

(12) United States Patent
Franz

(10) Patent No.: US 6,856,344 B2
(45) Date of Patent: Feb. 15, 2005

(54) VEHICLE UNDERCARRIAGE INSPECTION AND IMAGING METHOD AND SYSTEM

(76) Inventor: Robert H. Franz, 2504 N. Eagle La., Oklahoma City, OK (US) 73127

( * ) Notice: Subject to any disclaimer, the term of this patent is extended or adjusted under 35 U.S.C. 154(b) by 420 days.

(21) Appl. No.: 10/150,825

(22) Filed: May 17, 2002

(65) Prior Publication Data

US 2003/0185340 A1 Oct. 2, 2003

Related U.S. Application Data

(60) Provisional application No. 60/369,274, filed on Apr. 2, 2002.

(51) Int. Cl.$^7$ .............................................. H04N 7/18
(52) U.S. Cl. ..................................................... 348/143
(58) Field of Search .............................. 348/61–66, 77, 348/73, 82, 143–149, 158; 345/8; 134/6; H04N 7/18

(56) References Cited

U.S. PATENT DOCUMENTS

| | | | |
|---|---|---|---|
| 5,764,683 A | | 6/1998 | Swift |
| 5,769,954 A | * | 6/1998 | Wanner et al. .................. 134/6 |
| 5,805,209 A | | 9/1998 | Yuge |
| 5,974,111 A | | 10/1999 | Krug |
| 6,052,631 A | | 4/2000 | Busch |
| 6,249,567 B1 | | 6/2001 | Rothschild |
| 6,369,849 B1 | * | 4/2002 | Rzyski ......................... 348/61 |
| 2002/0097321 A1 | * | 7/2002 | McBride ..................... 348/148 |

OTHER PUBLICATIONS

"SecuScan—The Under Vehicle Monitoring System", Signalbau Huber, 8 pages.
"IR Range Finding for Mobile Robots", Les Williams, downloaded on Mar. 1, 2002 from http://www.cs.usc.edu, 12 pages.
"PC Video/USB Adapter Kit VA11A)", X10 Corporation, downloaded on Mar. 1, 2002 from http://www.x10.com, 2 pages.

"Xcam Wired Color Video Camera with 15'Cord", X10 Corporation, downloaded on Mar. 1, 2002 from http://www.x10.com, 4 pages.

"Fixed Site Under–Vehicle Inspection System (Waterproof)", papers M16–02 and M16–03, Law Enforcement Associates, Inc., 6 pages.

* cited by examiner

Primary Examiner—Tung Vo
(74) Attorney, Agent, or Firm—Robert H. Frantz

(57) ABSTRACT

A low-cost, portable and highly-mobile "speed bump" which incorporates a plurality of electronic cameras, illumination devices, and range finders. The system can be rapidly and temporarily deployed to achieve increased security at facilities and events likely to be terrorist targets, and at checkpoints to achieve an element of surprise to terrorists and smugglers. As a vehicle drives over the imaging speed bump, range finders measure the position of the vehicle wheels in order to properly mark the position at which various images are captured. Image frames are "stitched" together to form a complete image of the undercarriage for display to a guard, officer or soldier. Reference images for a particular make and model of vehicle, as well as previously captured images of a specific vehicle may be used to detect anomalies in the vehicle's undercarriage.

19 Claims, 19 Drawing Sheets

VEHICLE UNDERCARRIAGE INSPECTION AND IMAGING METHOD AND SYSTEM

CROSS-REFERENCE TO RELATED APPLICATIONS

This patent application is related to U.S. provisional patent application, Ser. No. 60/369,274, filed on Apr. 2, 2002, by Robert H. Frantz.

SPECIAL NOTE FOR REVIEW UNDER 35 U.S.C. 184 (MPEP 115)

REGARDING NATIONAL SECURITY ISSUES

This invention is provides a low cost, easy to use and highly mobile method for fully inspecting vehicle undercarriages for explosives and contraband. Should any Federal agency desire to procure the invention according to their own specifications, please contact the inventor for immediate action.

TECHNICAL FIELD OF THE INVENTION

This invention relates to the fields of anti-terrorism technology, security inspection equipment for vehicles, and law enforcement technology.

FEDERALLY SPONSORED RESEARCH AND DEVELOPMENT STATEMENT

This invention was not developed in conjunction with any Federally sponsored contract.

MICROFICHE APPENDIX

Not applicable.

INCORPORATION BY REFERENCE

The related patent application, U.S. provisional patent application Ser. No. 60/369,274, filed on Apr. 2, 2002, by Robert H. Frantz, is hereby incorporated by reference in its entirety, including figures.

BACKGROUND OF THE INVENTION

The undercarriages and underbodies of vehicles, including automobiles, vans and trucks, have become common places for criminals and terrorists to hide smuggled contraband, explosives, and even persons.

Along national borders, such as the U.S.-Mexican border, it is not uncommon for customs agents to discover packages of illegal drugs and narcotics bound to a portion of the structure of the undercarriage of a vehicle. In some cases, illegal immigrants have been discovered strapped underneath a vehicle. At entries to prisons and detention facilities, both scenarios have also transpired.

Terrorists, both domestically and abroad, have chosen the undercarriage of vehicles for their hiding place for explosives and detonation devices. Some terrorists attempt to drive a vehicle equipped with a bomb into an area, park the car, and leave it there for later detonation, while other "suicide" terrorist choose to detonate the explosives while they are still in the vehicle. These types of attacks have been carried out at national and international sporting events, in large parking facilities for targeted corporations, airports and train stations, embassies, border checkpoints, and other military and government installations.

For these reasons, many of these types of facilities have been equipped with guard stations where vehicles are stopped and inspected, as shown in FIG. 3. In this portrayal of the typical undercarriage inspection process (30), a guard or soldier (33) will use a mirror (34) mounted on a long handle with wheels (35) to manually and visually inspect the undercarriage (32) of a vehicle (31). The inspection device may be equipped with a flashlight (36) to illuminate the underside of the vehicle through reflection in the mirror (34). The guard will move around the periphery of the vehicle, maneuvering the wheeled mirror so as to inspect most aspects, features and structures under the car.

While this process is very inexpensive and portable, several difficulties and potentially fatal flaws exist with the system. First, the undercarriages of vehicles are extremely "busy" and complicated structures, having hundreds of features such as suspension components, fuel lines and tanks, floorpans, brake components, exhaust manifolds and pipes, mufflers, differentials and constant-velocity joints, transmission case details, etc. As each make and model of vehicle is different, a guard cannot realistically detect features under the vehicle which are not normal, altered, or added unless they exhibit some obvious characteristics (shiny instead of dirty, hanging loose, etc.). As such, a savvy terrorist or smuggler can mask a package of contraband or explosives to evade this type of manual inspection fairly easily.

At least one system has been developed to assist in a more thorough, automated and computer-assisted inspection of vehicle undercarriages. This system requires installation "below grade" or below the surface level on which the vehicle travels. This type of permanent installation is effective for facilities which are considered a permanent target or are a common entry point to a border or prison, in that it may be incorporated into the guard station construction in the driveway passing by the guard's booth. Most of these types of systems also require some cooperation by the driver, such as following a traffic signal to stop the vehicle and advance the vehicle when the equipment is ready for additional scanning and imaging.

As these type of permanent installations can be easily seen and anticipated by terrorists and smugglers, they may simply adjust their plans to work around the permanent inspection point, such as plot an attack on another target or look for a vulnerable point to access the facility without going through the guard booth (e.g. crash a weak fence).

Additionally, these types of permanently-installed systems may be subject to weather conditions such as rain and snow, unless they are installed under an awning or roof and are kept clean.

Further, there are many scenarios where the security risk or threat is temporary in nature, but to which a response must be made quickly—more quickly than the time needed to plant a scanning and imaging device into a roadway or driveway. For example, a sporting event such as the American SuperBowl occurs at different venues each year, so permanently installing a below-grade scanning system is not cost efficient. The same is true of international sporting events, such as the Olympic games and regional and international soccer championships. Still other examples are conventions and diplomatic meetings at hotels and conference centers which draw threats of violence, visits of dignitaries to public and government facilities, temporary stationing of military personnel in make-shift barracks (domestically and abroad), etc. In these cases, the best solution available to date has been the manual rolling-mirror process.

One available solution provided by Singalbau Huber of Germany utilizes a reflective camera bay which is placed in a shallow trench approximately 12" (30 cm) below grade. The cameras are placed in a horizontal viewing position such that they have a perspective at a mirror which is set at an angle to look out of a slit in the roadway towards the underbody of a vehicle. Induction loops, such as those used to detect vehicles at traffic signals and intersections, are placed in front of and behind the camera bay in order to detect when a vehicle is present, and to estimate the speed of the vehicle. A traffic light is integrated into the system, which allows a cooperative driver to advance his vehicle across the viewing slit.

This system provides some solution to the problems in the art, but in part depends on the use of the induction loops which are known in the art to have reliability problems, and in part depends on installation below grade approximately 12", reducing its portability.

Therefore, there exists a need in the art for a vehicle undercarriage imaging and inspection system which is portable and can be quickly deployed to respond to changing threat conditions and scenarios. Additionally, there exists a need for this system to provide self-contained illumination, and preferably non-visible illumination such as infrared light, to assist in the inspection of undercarriages regardless of ambient lighting conditions. Further, there exists a need in the art for this system to be highly mobile so that would-be terrorists and smugglers are not able to anticipate the location of inspection points, thereby thwarting their efforts and counter-measures. There also exists a need in the art for computer-assisted inspection to look for non-standard, non-stock features on the vehicle, compared both to known manufacturers' configurations as well as specific configurations for specific vehicles, in order to increase the likelihood of detection an altered or added structure under a vehicle.

Finally, there exists a need in the art for this new system to allow for remote expert analysis and consultation to be employed in cases of questionable undercarriage structures and configurations in order to decrease false alarms and increase the reliability with which the operators view the system.

SUMMARY OF THE INVENTION

The invention provides a portable, mobile "speed bump" which incorporates a plurality of solid-state cameras, illumination devices, and range finders. As a vehicle drives over the speed bump, range finders measure the position of the front and/or rear wheels in order to properly mark the position at which various images are made using the cameras. Digital images are transferred to a computing platform, such as a laptop computer, where they are "stitched" together to form a complete and whole image of the undercarriage, and where they can be viewed by a guard, officer or soldier.

In an enhanced embodiment, the make and model of the vehicle is determined and a reference undercarriage image is compared to the image taken of the vehicle being inspected, with differences being designated on the system display to alert the operator to the potential threat. In another enhanced embodiment, undercarriage images may be stored for specific vehicles and later retrieved for use a reference image for that vehicle, such as cars and trucks which regularly enter a government complex or military base, which further increases the accuracy of the comparison and likelihood of detecting modified and added structures.

In another enhancement of the present invention, remote "experts" may receive actual images taken under a vehicle so that they may make a more accurate determination as to anomalies detected by the comparison of reference images to actual images. These experts may include "factory trained" technicians for specific makes and models of vehicles, as well as demolitions and counter-terrorism experts.

As such, the invention is highly portable and mobile, quick to deploy and easy to operate, allowing its use temporarily at potential target venues such as sporting events, conventions and conferences, and dignitary proceedings. Further, it is suitable for surprise operations, such as roadblocks and random entry point searches, thereby keeping would-be smugglers and terrorists from being able to anticipate the location of the inspection equipment and to adjust accordingly.

BRIEF DESCRIPTION OF THE DRAWINGS

The figures presented herein when taken in conjunction with the disclosure form a complete description of the invention.

DETAILED DESCRIPTION OF THE INVENTION

The invention has several components and portions, one of which is a common computing platform for providing certain image processing functions and providing the user or operator with a display on which a vehicle's undercarriage may be viewed. These common computing platforms can include personal computers as well as portable computing platforms, such as personal digital assistants ("PDA"), web-enabled wireless telephones, and other types of personal information management ("PIM") devices.

Therefore, it is useful to review a generalized architecture of a computing platform which may span the range of implementation, from a high-end web or enterprise server platform, to a personal computer, to a portable PDA or web-enabled wireless phone.

Figure 1:
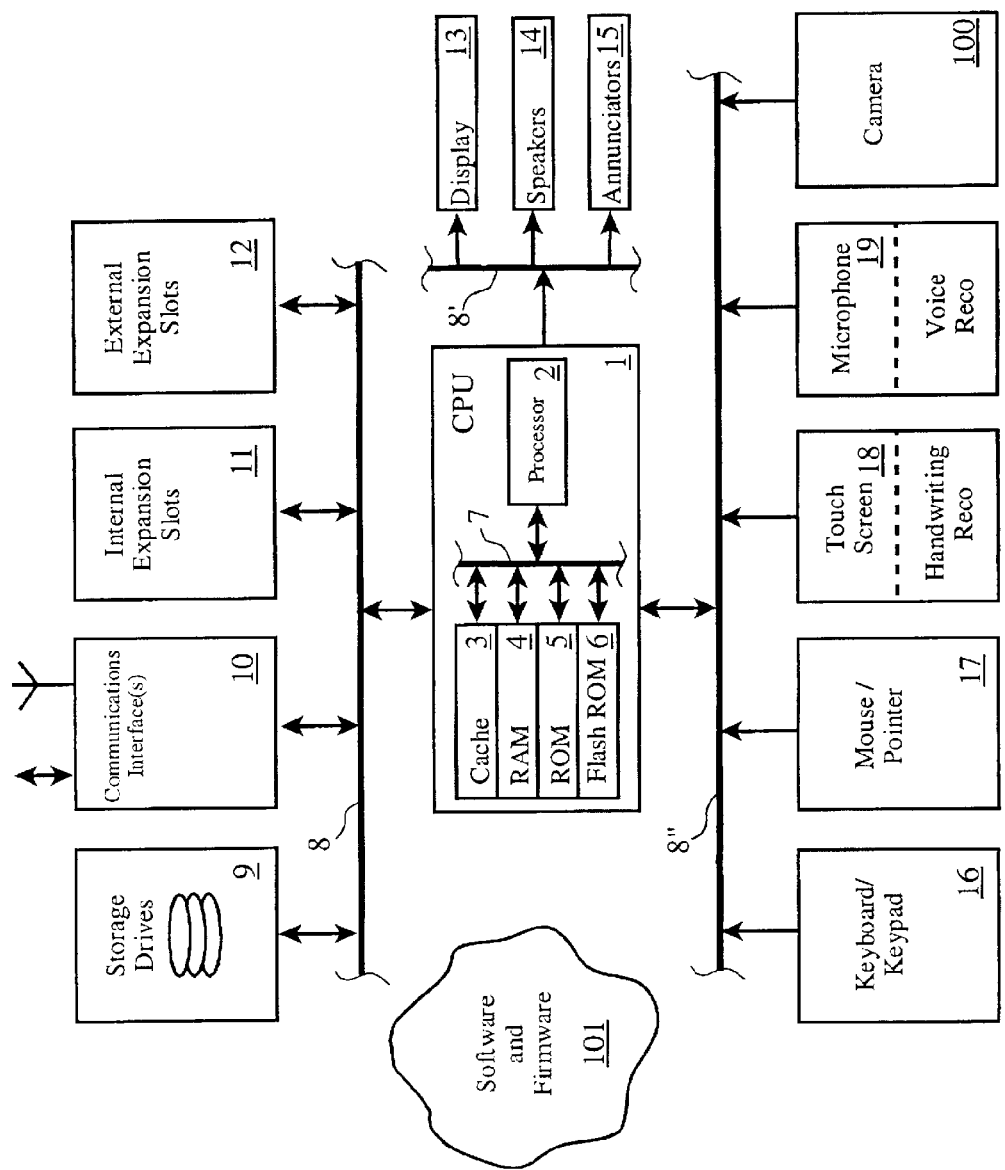
FIG. 1 depicts a generalized computing platform architecture, such as a personal computer, server computer, personal digital assistant, web-enabled wireless telephone, or other processor-based device.

Turning to FIG. 1, a generalized architecture is presented including a central processing unit (1) ("CPU"), which is typically comprised of a microprocessor (2) associated with random access memory ("RAM") (4) and read-only memory ("ROM") (5). Often, the CPU (1) is also provided with cache memory (3) and programmable FlashROM (6). The interface (7) between the microprocessor (2) and the various types of CPU memory is often referred to as a "local bus", but also may be a more generic or industry standard bus.

Many computing platforms are also provided with one or more storage drives (9), such as a hard-disk drives ("HDD"), floppy disk drives, compact disc drives (CD, CD-R, CD-RW, DVD, DVD-R, etc.), and proprietary disk and tape drives (e.g., Iomega Zip [TM] and Jaz [TM], Addonics SuperDisk [TM], etc.). Additionally, some storage drives may be accessible over a computer network.

Many computing platforms are provided with one or more communication interfaces (10), according to the function intended of the computing platform. For example, a personal computer is often provided with a high speed serial port (RS-232, RS-422, etc.), an enhanced parallel port ("EPP"), and one or more universal serial bus ("USB") ports. The computing platform may also be provided with a local area network ("LAN") interface, such as an Ethernet card, and other high-speed interfaces such as the High Performance Serial Bus IEEE-1394.

Computing platforms such as wireless telephones and wireless networked PDA's may also be provided with a radio frequency ("RF") interface with antenna, as well. In some cases, the computing platform may be provided with an infrared data arrangement (IrDA) interface, too.

Computing platforms are often equipped with one or more internal expansion slots (11), such as Industry Standard Architecture (ISA), Enhanced Industry Standard Architecture (EISA), Peripheral Component Interconnect (PCI), or proprietary interface slots for the addition of other hardware, such as sound cards, memory boards, and graphics accelerators.

Additionally, many units, such as laptop computers and PDA's, are provided with one or more external expansion slots (12) allowing the user the ability to easily install and remove hardware expansion devices, such as PCMCIA cards, SmartMedia cards, and various proprietary modules such as removable hard drives, CD drives, and floppy drives.

Often, the storage drives (9), communication interfaces (10), internal expansion slots (11) and external expansion slots (12) are interconnected with the CPU (1) via a standard or industry open bus architecture (8), such as ISA, EISA, or PCI. In many cases, the bus (8) may be of a proprietary design.

A computing platform is usually provided with one or more user input devices, such as a keyboard or a keypad (16), and mouse or pointer device (17), and/or a touch-screen display (18). In the case of a personal computer, a full size keyboard is often provided along with a mouse or pointer device, such as a track ball or TrackPoint [TM]. In the case of a web-enabled wireless telephone, a simple keypad may be provided with one or more function-specific keys. In the case of a PDA, a touch-screen (18) is usually provided, often with handwriting recognition capabilities.

Additionally, a microphone (19), such as the microphone of a web-enabled wireless telephone or the microphone of a personal computer, is supplied with the computing platform. This microphone may be used for simply reporting audio and voice signals, and it may also be used for entering user choices, such as voice navigation of web sites or auto-dialing telephone numbers, using voice recognition capabilities.

Many computing platforms are also equipped with a camera device (100), such as a still digital camera or full motion video digital camera.

One or more user output devices, such as a display (13), are also provided with most computing platforms. The display (13) may take many forms, including a Cathode Ray Tube ("CRT"), a Thin Flat Transistor ("TFT") array, or a simple set of light emitting diodes ("LED") or liquid crystal display ("LCD") indicators.

One or more speakers (14) and/or annunciators (15) are often associated with computing platforms, too. The speakers (14) may be used to reproduce audio and music, such as the speaker of a wireless telephone or the speakers of a personal computer. Annunciators (15) may take the form of simple beep emitters or buzzers, commonly found on certain devices such as PDAs and PIMs.

These user input and output devices may be directly interconnected (8', 8") to the CPU (1) via a proprietary bus structure and/or interfaces, or they may be interconnected through one or more industry open buses such as ISA, EISA, PCI, etc. The computing platform is also provided with one or more software and firmware (101) programs to implement the desired functionality of the computing platforms.

Figure 2:
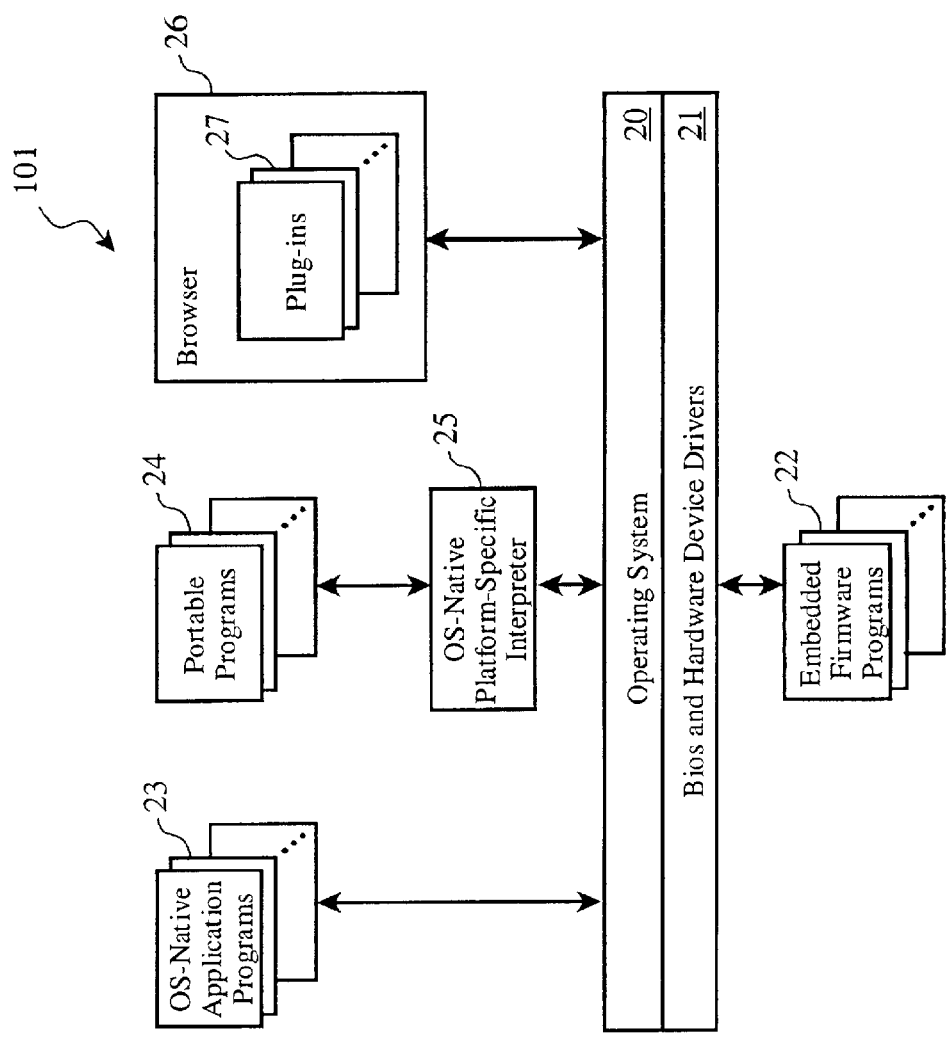
FIG. 2 shows a generalized organization of software and firmware associated with the generalized architecture of FIG. 1.
Figure 3:
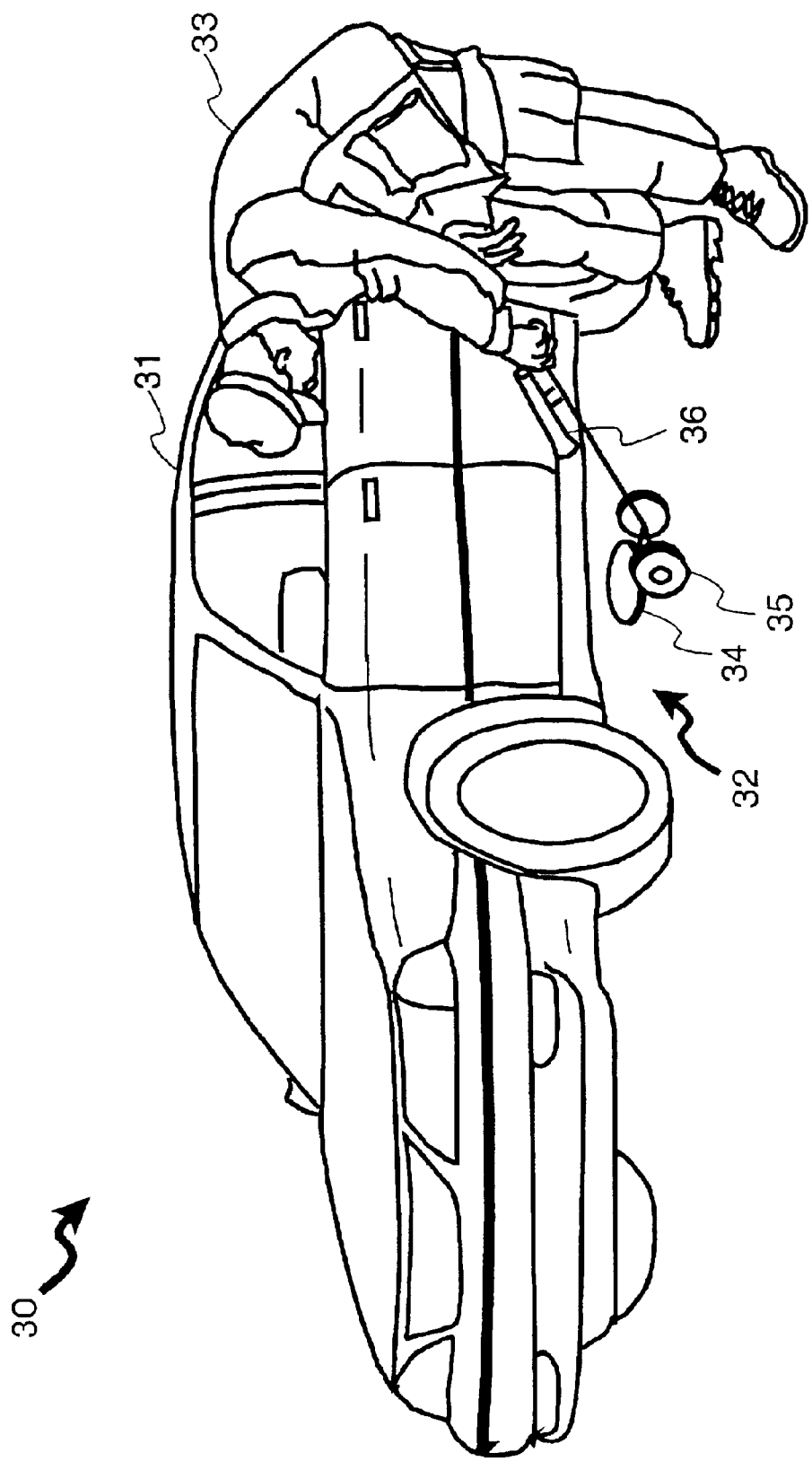
FIG. 3 illustrates the current manual inspection method for searching an undercarriage of a vehicle.

Turning to now FIG. 2, more detail is given of a generalized organization of software and firmware (101) on this range of computing platforms. One or more operating system ("OS")-native application programs (23) may be provided on the computing platform, such as word processors, spreadsheets, contact management utilities, address book, calendar, email client, presentation, financial and bookkeeping programs.

Additionally, one or more "portable" or device-independent programs (24) may be provided, which must be interpreted by an OS-native platform-specific interpreter (25), such as Java [TM] scripts and programs.

Often, computing platforms are also provided with a form of web browser or micro-browser (26), which may also include one or more extensions to the browser such as browser plug-ins (27).

The computing device is often provided with an operating system (20), such as Microsoft Windows [TM], UNIX, IBM's OS/2 [TM] and AIX [TM], LINUX, MAC OS [TM] or other platform specific operating systems. Smaller devices such as PDA's and wireless telephones may be equipped with other forms of operating systems such as real-time operating systems ("RTOS"), or a portable computer operating system such as Palm Computing's PalmOS [TM] or Microsoft's Windows CE [TM].

A set of basic input and output functions ("BIOS") and hardware device drivers (21) are often provided to allow the operating system (20) and programs to interface to and control the specific hardware functions provided with the computing platform.

Additionally, one or more embedded firmware programs (22) are commonly provided with many computing platforms, which are executed by onboard or "embedded" microprocessors as part of the peripheral device, such as a microcontroller for a hard drive, a communication processor, network interface card, or sound or graphics card.

As such, FIGS. 1 and 2 describe in a general sense the various hardware components, software and firmware programs of a wide variety of computing platforms, including but not limited to personal computers, PDAs, PIMs, web-enabled telephones, and other appliances such as WebTV [TM] units. We now turn our attention to disclosure of the present invention relative to other hardware, processes and methods of the invention, preferably implemented as peripherals to and software on such a computing platform. It will be readily recognized by those skilled in the art that the following methods and processes may be alternatively realized as hardware functions, in part or in whole, without departing from the spirit and scope of the invention.

Imaging Bar Architecture and Operation

Figure 4:
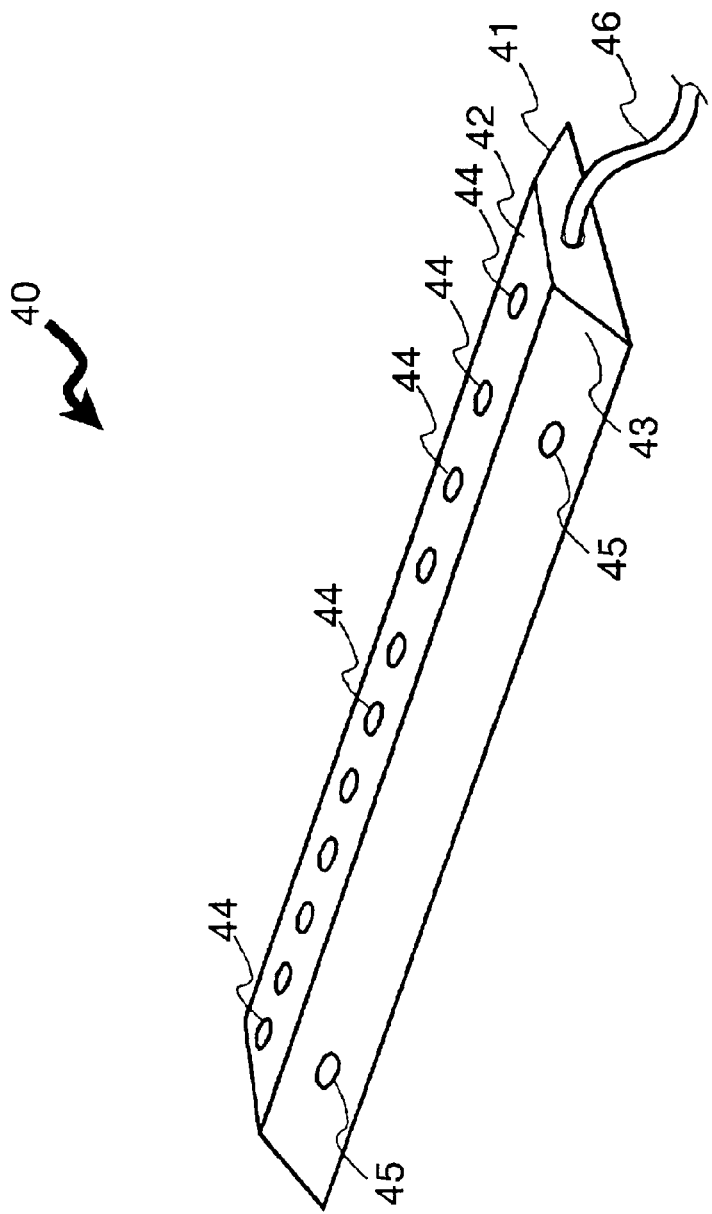
FIG. 4 discloses the form factor of the imaging "bar" or "speed bump" of the present invention according to a preferred embodiment.

Turning now to FIG. 4, the imaging bar is of the invention is disclosed in detail. The preferred embodiment is to provide an imaging bar (40) with a generally trapezoidal cross-sectional shape, having a rear surface (41), top surface (42), and front surface (43). Lengthwise along the top surface are disposed a plurality of camera portals or apertures (44), through which upward-looking cameras may gain a perspective of the undercarriage of a vehicle while it passes over the imaging bar (40). Disposed in the front edge (45) and the rear edge (not shown) along the general area corresponding to the wheel track of an average vehicle are range finder portals (45), as well. An instrumentation lead (46) is provided for interconnection of the imaging bar (40) to a power supply (battery, AC adapter, etc.), video displays, recorders, and/or a computing platform.

In general, the dimensions of the imaging bar (40) are to be slightly longer than the average width of a car or truck to be inspected, but not longer than the width of an ordinary lane of traffic (unless a multiple-lane imaging bar is to be realized). A length of 80 inches to 90 inches will suffice for most applications. The depth of the imaging bar, measured from front surface leading edge to rear surface trailing edge, can be selected according to the dimensions of the electronic components housed within the imaging bar. The slope (or curvature) of the front surface and rear surface should be suitable to allow a vehicle to pass over the imaging bar at a moderate speed, such as 5 MPH, without posing a threat of losing control of the vehicle. Alternate dimensions and slopes may be employed according to the intended circumstances, such as creating a very deep unit with a very slight slope on the front and rear surfaces to allow the imaging and scanning of vehicles as the pass over the imaging bar at greater speeds, of course. The housing may be constructed of plastic (recycled plastics, PVC, resin, etc.) or sheet metal (rolled steel, aluminum, etc.), such as plastic speed bumps offered readily on the market from companies such as Plastic Safety Systems, Inc., and SealMaster Industries, Inc.

Figure 5:
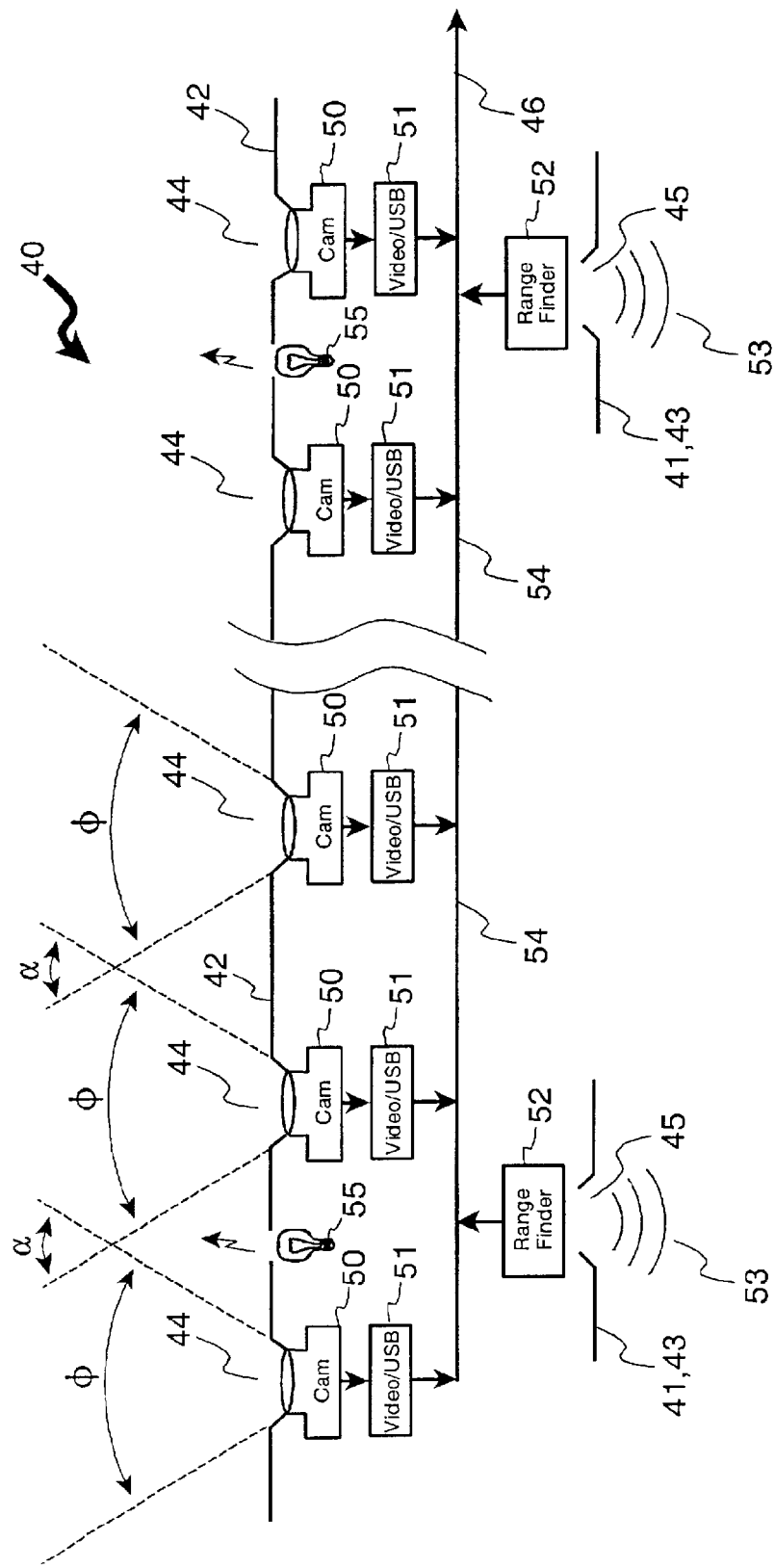
FIG. 5 provides architectural and electronic details of the preferred embodiment of the imaging bar.

In FIG. 5, the internal architecture according to a preferred embodiment of the imaging bar (40) is shown. This architecture is but one of many possible architectures, with this particular architecture assuming the functionality of a USB computer peripheral. A number of miniature digital cameras (50) are arranged underneath the top surface of the imaging bar such that they have a perspective looking upwards and out of each camera portal (44). Such a miniature camera is X-10 corporation's inexpensive Xcam, which provides fairly high resolution color images in an extremely small package, or Pelikan Industries' series of ultra-mini color and black and white cameras.

The field of view (FOV), $\phi$ (phi), of such a camera is approximately 60 to 90 degrees, depending on the model of camera. The cameras are arranged with a spacing between cameras such that overlaps $\alpha$ (alpha) of their fields of view are achieved at a distance similar to the intended ground-to-chassis clearance of the vehicle to be inspected. This overlap will produce similar features within images from adjacent cameras, which is used in the image processing steps described later. For imaging only trucks which have a greater ground clearance, fewer cameras with greater camera-to-camera spacing may be employed. Conversely, if imaging only automobiles, more cameras with closer spacing may be employed, or alternate cameras with wider fields of view may be employed. For imaging a wide variety of vehicles such as cars, trucks and vans, the camera spacing is preferably made to accommodate the vehicle with the lowest ground clearance. More details for the ideal spacing between cameras according to the preferred embodiment are presented later in this disclosure.

Further according to the preferred embodiment, a converter for placing the camera video signals onto a USB bus is provided, such as X-10 corporation's PC Video/USB Adapter Kit. Alternate camera choices, though, may be directly compatible with USB without such a special adapter, and it is within the skill of those in the art to select such substitutions. The digital camera video outputs are then placed onto a main bus (54), which is then transmitted out the instrumentation lead (46).

Alternate embodiments are available for this portion of the invention, including use of alternate computer bus technologies (PCI, "FireWire", RS-422, Ethernet), or more "analog" solutions such as a use of a muti-port video signal selector.

The imaging bar (40) is also preferably provided with two range finders (52) on the front surface, and two range finders (52) on the rear surface. These are preferably placed towards the left and right ends of the imaging bar generally in the wheel track of a common vehicle, such as 75" apart. The range finders (52) are situated such that they may "view" the treads of the vehicle under inspection through the range finder portals (45). These devices may be the common ultrasonic type ordinarily found in auto-focus cameras and digital tape measures, suitably chosen for accuracy within a few fractions of an inch at a range from point blank to a few feet, as will be described in the following paragraphs. Some ultrasonic and laser-based range finders are readily available on the market as a personal computer peripheral, such as Massa Products Corporation's ultrasonic M5000/95 unit which supports interfacing to a computer via a multi-drop RS-485 bus.

Preferably, the range readings of the range finders are also placed on the main bus (54) such that they are available to a computer for use in determining the position of the vehicle with each frame of image collected from each camera.

Alternate range finding technologies may be employed, of course, such as laser-based range finders, according to the intended application for the imaging bar.

Further according to the preferred embodiment, one or more sources of illumination are provided along the top of the imaging bar, such as visible-light lamp bulbs, light emitting diodes, or Infrared light sources. This may be used to enhance the illumination of the features and components of the vehicle's undercarriage, and to offset lack of sensitivity of the cameras' imaging technology. If low-light (low-lux) cameras are employed, the additional illumination devices may not be necessary.

Figure 19:
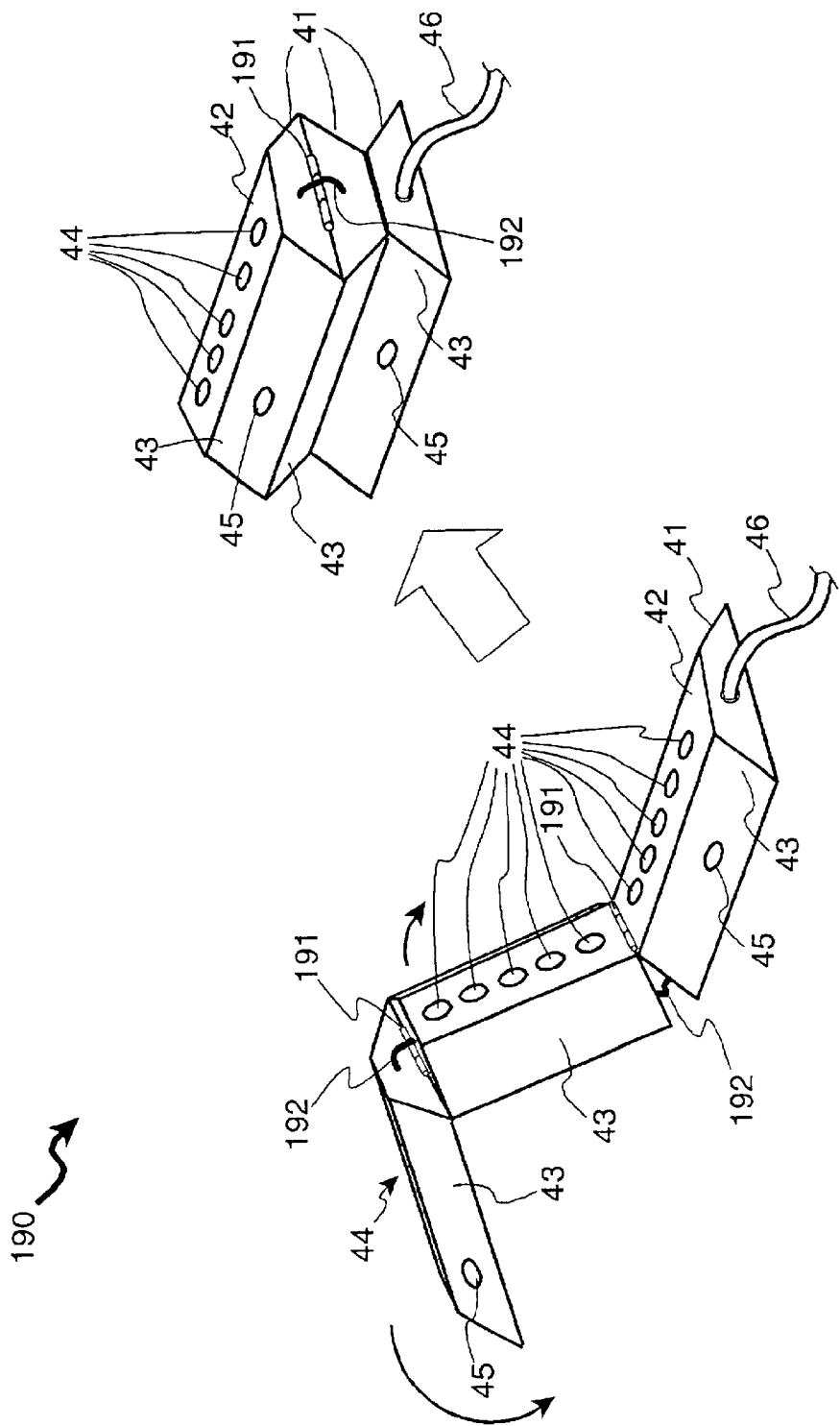
FIG. 19 shows the folding mechanisms of the preferred embodiment to provide enhanced portability.

FIG. 19 illustrates an alternate mechanical embodiment (190) which provides even greater portability, by allowing the imaging bar to fold into multiple sections and stack upon itself. One or more hinges (191) may be provided between the sections, with an appropriate electronic cable (192) such as a set of cables in a flexible protective sheath, a ribbon cable or a flex circuit. While the single-section unit would likely be approximately 80 inches in length, requiring a pick up, trailer, or sedan equipped with a roof rack to transport, the folding embodiment (192) may be reduced to one-half or less of that length for transport in the trunk of a typical car, such as 27 inches.

Figure 6:
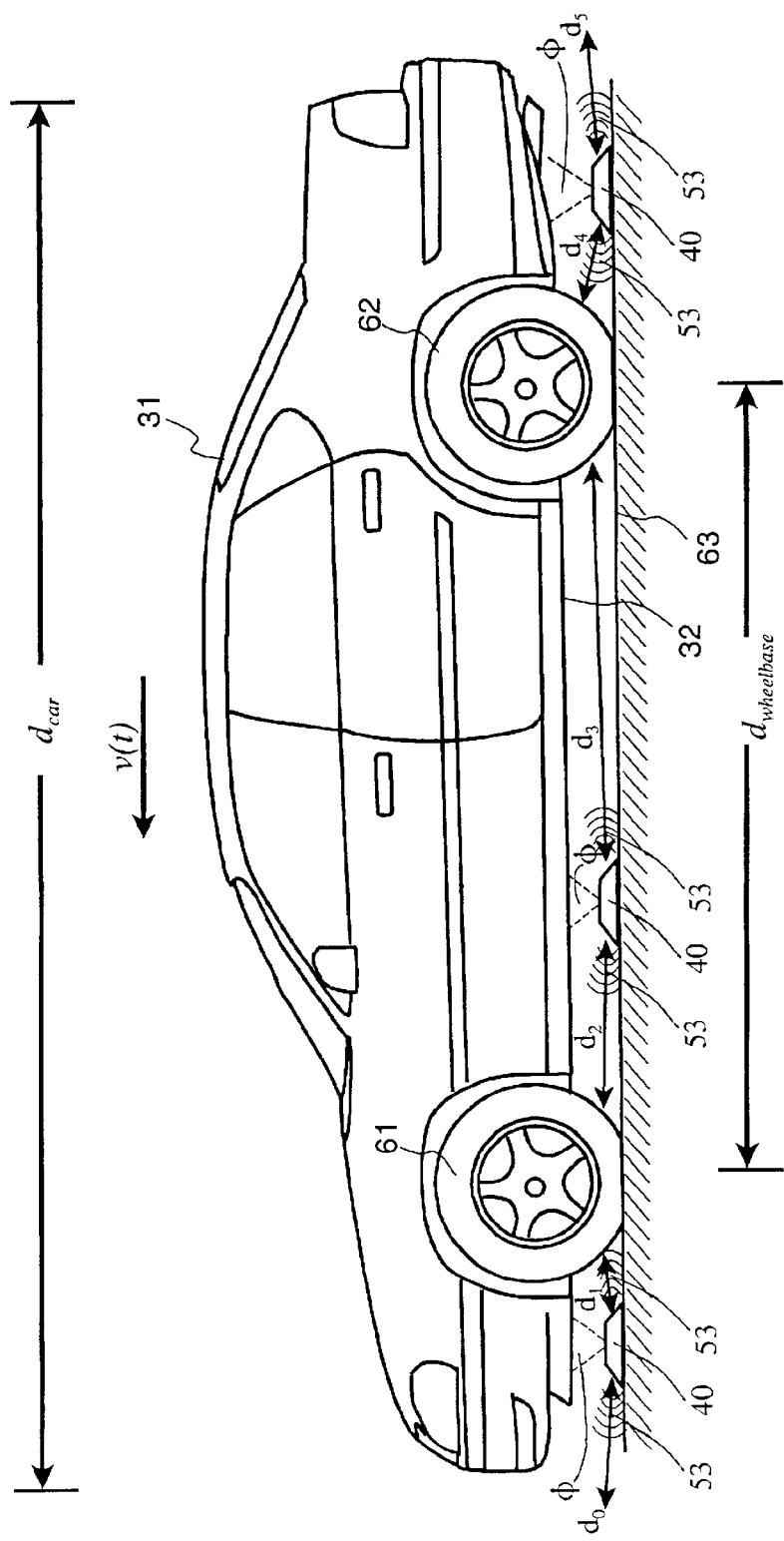
FIG. 6 shows the three relative positions of the imaging bar as a vehicle passes over it, with the bar (1) in front of the front wheels, (2) between the front and rear wheels, and (3) behind the rear wheels.

Turning now to FIG. 6, the method of use of the imaging bar is illustrated. The imaging bar (40) placed across a lane of traffic, such as a parking lot entry drive, guard booth driveway, roadway, or entrance to a facility (military base, government building, etc.). The form factor previously described is of dimensions which are easily moved and transported by a single adult, and stored easily in the bed of a truck or trunk of an automobile. The imaging bar is completely self-contained single unit, according to the preferred embodiment, needing no signal lights or driver cooperation, separate induction loops, or below-grade construction or preparation.

As the vehicle (31) is driven towards the imaging bar (40) with a time varying velocity v(t) according to the driver's control, the imaging bar comes under the front portion of the vehicle (31) in front of the front wheels (61). During this phase of imaging, the front range finders will not receive a response or measurement $d_0$ that falls within the normal range of a vehicle wheelbase, and the rear range finder will make a measurement $d_1$ to the front tread of the front tire (61). For this first phase of imaging, the speed of the vehicle v(t) can be determined by repeated, timed measurements of the distance $d_1$ from the rear range finder to the front wheel (61), using a calculation such as:

$$\Delta d \div \Delta t = v(t_i)$$

where $\Delta d$ is the change in position or distance between timed measurements, $\Delta t$ is the change in time between two consecutive measures, and $v(t_i)$ is the calculated velocity of the vehicle for the $i^{th}$ set of images.

Several frames of image may be taken and stored from each camera during this phase such that some portion of each image overlaps $\alpha$ with the previous image from the same camera, based upon the known field of view $\phi$ of the cameras and the determined speed of the vehicle during this phase.

After the front wheels pass over the imaging bar (40), a second phase of imaging is entered as the vehicle (31) straddles the imaging bar with front wheels in front of the front surface of the imaging bar and the rear wheels still behind the imaging bar. In this second phase of imaging, the front range finder will measure the distance $d_2$ to the rear tread of the front wheel (61), and the rear range finder will measure the distance $d_3$ to the front tread of the rear wheel (62).

As in the first phase of imaging, periodic timed measurements of $d_2$ and $d_3$ can be made using the range finders to determine the time-variant speed v(t) and position of the vehicle for each frame of image taken from the cameras, and to allow appropriately timed frames to be captured having image overlaps $\alpha$ in the fields of view $\phi$ for successive images from the same camera, as explained in more detail in the following paragraphs.

In this phase, however, the total distance between wheels is approximately the wheelbase of the vehicle, and as $d_2$ increases, $d_3$ will decrease according to the equation:

$$d_{wheelbase} = d_2 + d_3 + (\text{width of the imaging bar})$$

This wheelbase measurement may be used to assist in classifying the vehicle because known makes and models each have a specified wheelbase measurement that is rarely modified after delivery of the vehicle.

During a third and final phase of imaging, the vehicle's rear wheels (62) pass over the imaging bar (40) such that the rear range finder now returns a high or infinite distance $d_5$, and the front range finder provides a real time distance measurement d4 to the rear tread of the rear tire (62).

As in the first and second phases of imaging, periodic timed measurements of $d_4$ can be made using the front range finder to determine the time-variant speed v(t) of the vehicle for each frame of image taken from the cameras, and to allow appropriately timed frames to be captured having image overlaps $\alpha$ in the fields of view $\phi$ for successive images from the same camera.

Since the speed v(t) of the vehicle (31) is determined using the range finders for each image frame captured, and the actual wheelbase of the vehicle is measured, the composite image produced by the image composition process (described later) can be used to determine the front bumper to rear bumper length of the vehicle $d_{car}$, which can also be used with the wheelbase measurement to classify the vehicle as to make and model.

Figure 7:
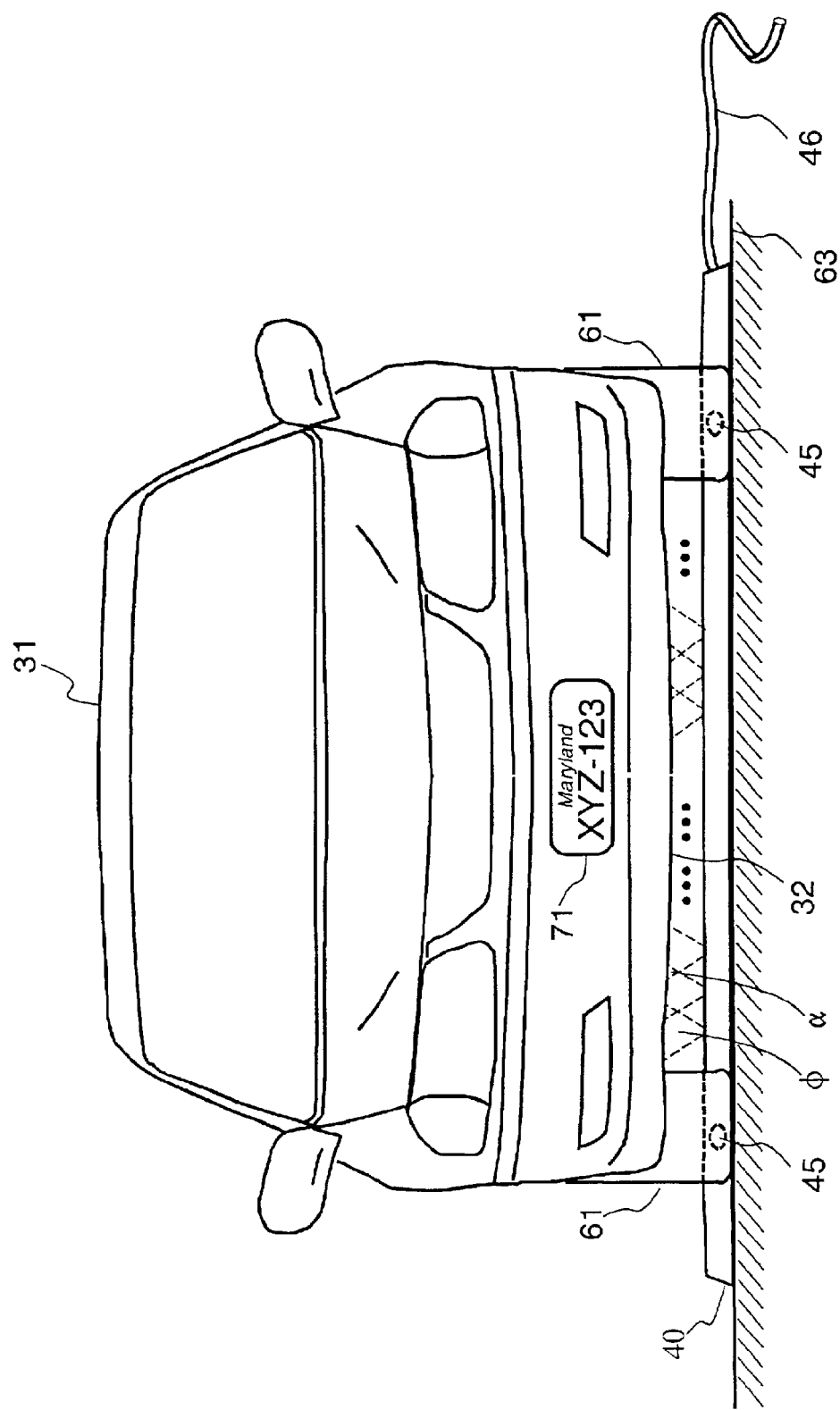
FIG. 7 shows a frontal view of the imaging bar while underneath a vehicle.

Turning to FIG. 7, a front view of a vehicle (31) is shown in the second or third phase of imaging. In this view, the range finder positions (45) in the wheel tracks are evident, as are the side-to-side imaging fields of view $\phi$ and image overlaps $\alpha$ are shown. The instrumentation lead (46) is preferably dressed away from the path of travel of the vehicle to avoid possible entanglement with the vehicle and damage by the vehicle tires.

Figure 14:
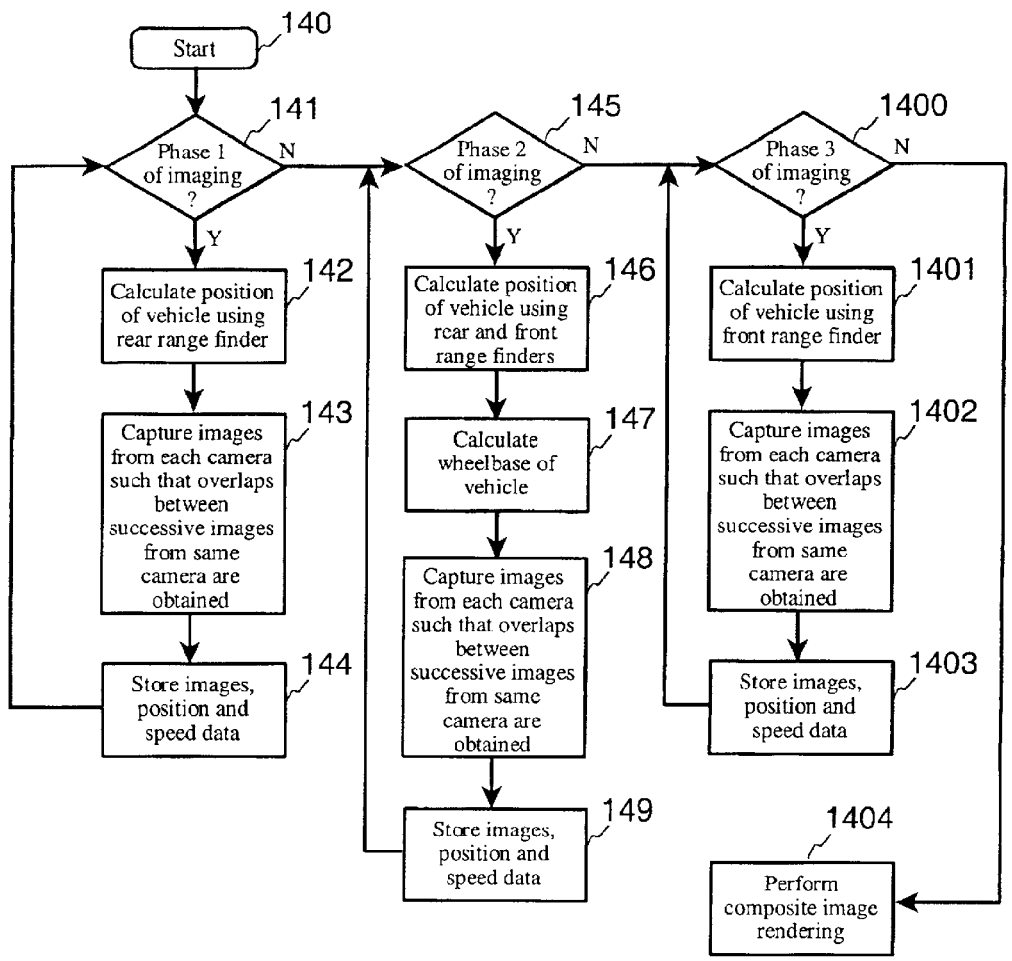
FIG. 14 shows the logical process of the invention for obtaining image frames from the cameras in the imaging bar.

FIG. 14 depicts the logical process of capturing frames of images from the cameras as just described, wherein phase 1 (141–144) uses only the rear range finder to calculate vehicle speed and position, and to time the capturing of image frames; in phase 2 (145–149) both range finders are used to calculate vehicle position and velocity, as well as to determine vehicle wheelbase, and to time the capturing of image frames; and in phase 3 (1400–1404) during which only the front range finder is used to calculate vehicle speed and position, and to time the capturing of image frames.

System Architecture

Figure 8:
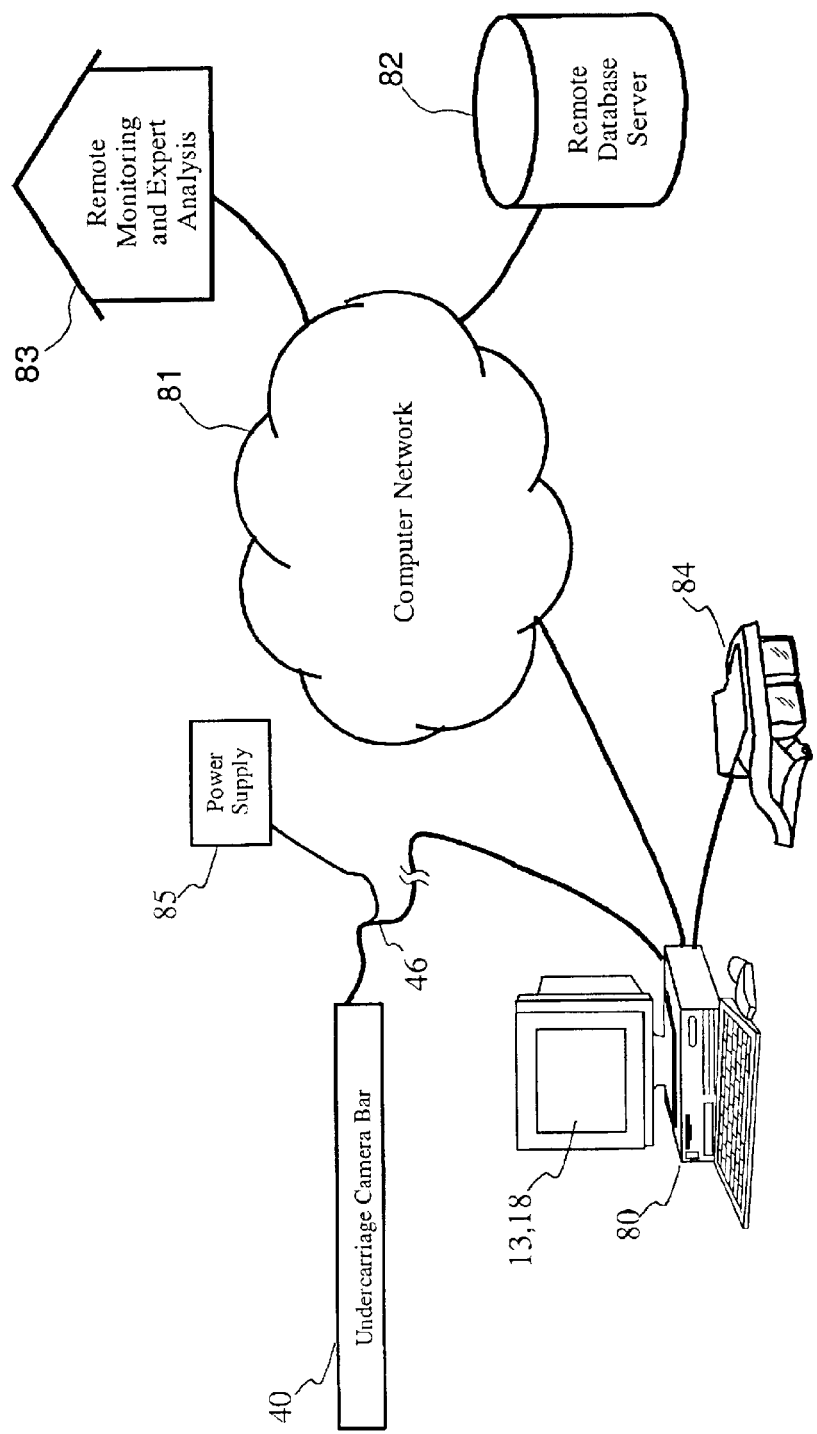
FIG. 8 illustrates the components of the invention employed in conjunction with the imaging bar.

A computing platform (80) such as those previously described is preferably interconnected to the imaging bar (40) via the instrumentation lead (46), as shown in FIG. 8. According to the preferred embodiment, the instrumentation lead (46) comprises one or more USB signals and a multi-drop RS-485 bus, but could equally well comprise alternate digital busses (e.g. Ethernet, FireWire, etc.), and it includes an interconnect to a power supply (85) such as a battery, vehicle power source, or AC/DC adapter. The computing platform (80) is equipped with an appropriate interface to the instrumentation lead (46) such that software running on the computing platform may receive and store frames of image from the cameras in real time, as well as receive and store the range finder measurements in real time.

Using the stored image frames and distance measurements associated with each frame, the software can perform the processes described in the following paragraphs.

In a fundamental embodiment of the invention, the rendered composite image of the vehicle undercarriage may be displayed on the computing platform's display (13, 18), such as a laptop computer display, a desktop or workstation computer's CRT, or even a display on a PDA. In a more advanced embodiment for closer inspection and/or use in bright light environments (e.g. outdoors), a set of 3-dimensional "virtual reality" viewing glasses (84) may be driven by the computer via special digital outputs or standard video outputs. Such 3-D glasses are readily available in the gaming industry, such as the MindFlux Corporation's "i-Glasses".

In an even more advanced embodiment, the computing platform may be connected to a computer network, such as a wireless network, local area network or the Internet, using common network means (LAN interfaces, wireless networking interfaces), to provide connectivity to remote analysis experts and/or remote database storage, the use of which is described in more detail in the following paragraphs.

Composite Image Rendering Process

We now turn our attention to description of the methods of the invention which are preferably realized as standalone software application programs, such as Microsoft Windows [TM], Linux or Palm OS programs.

To illustrate the composite image rendering process of the invention, we first present for reference a simplified view of an automobile undercarriage. In practice, the photographed image of a vehicle undercarriage would appear in greater detail, in black and white or color. The simplified view as presented in FIG. 9 is used for this illustration in order to increase ease of understanding the invention.

Figure 9:
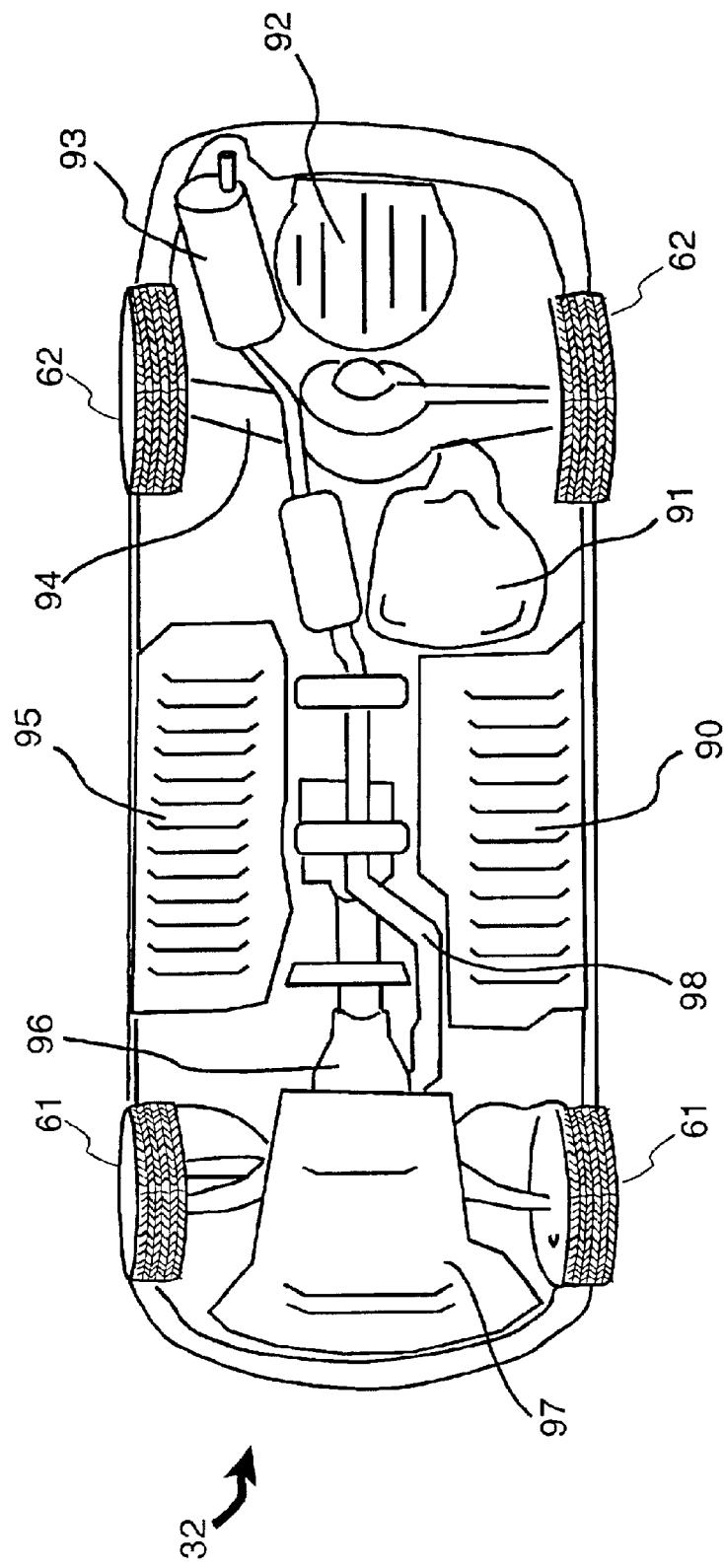
FIG. 9 provides a simplified image of an automobile undercarriage for use in illustrating the image processing functions of the invention.

In FIG. 9, certain details of the undercarriage (32) of a car are shown, including the passenger side floor pan (90), the fuel tank (91), two rear tires (62), an outline of the spare tire in the trunk area (92), a muffler (93), portions of the rear suspension (94), a driver side floor pan (95), a portion of the engine drive shaft output (96), two front tires (61), a front skid plate (97), and a portion of the exhaust system (98).

Figure 10:
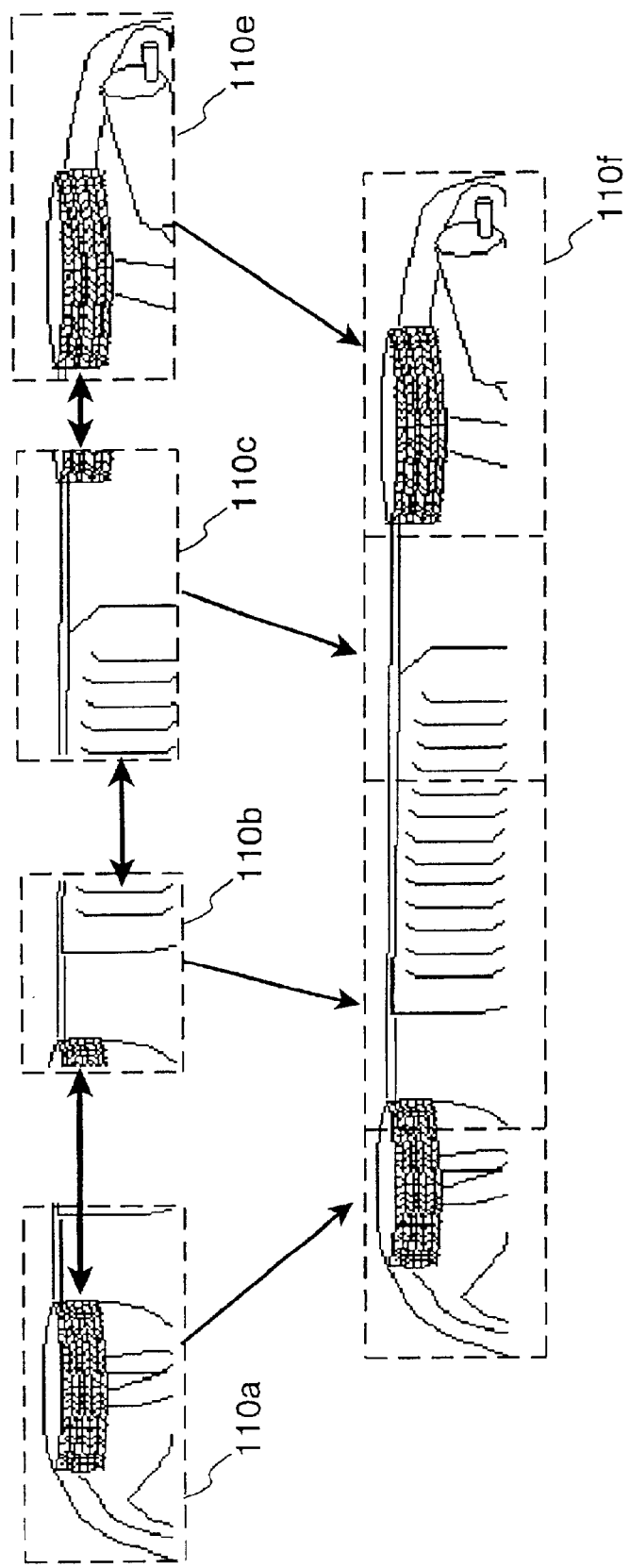
FIG. 10 depicts the image processing functions as they take multiple "tiles" or photographic shots from a single camera, find edge features, and create a "strip" photo comprising multiple shots from a single camera.

Turning to FIG. 10, a sample group of image frames taken from one camera in the imaging bar (110a, 110b, 110c, and 110e) are shown. As can be seen by the details pointed to by the double headed arrows in FIG. 10, each separate image frame contains a portion of common image features towards the edges of the frames adjacent to each other. These areas of common features in each frame result from the overlapping camera fields of view α described earlier.

According to the present invention, the composite image rendering software finds the common features in sequential adjacent image frames (from the same camera) in order to stitch them together to create a strip photo (110f), as shown.

Image feature extraction for image processing is well owned in the art. Our method for generating overlapping image (described in the following paragraphs) greatly enhances the ability of the image processor to find common features in adjacent images, as the method results in sequential images and adjacent images which definitely have a portion overlapping with each other containing common features. As such, one method for finding these features is to perform a comparison between the edge regions of adjacent frames.

Figure 11:
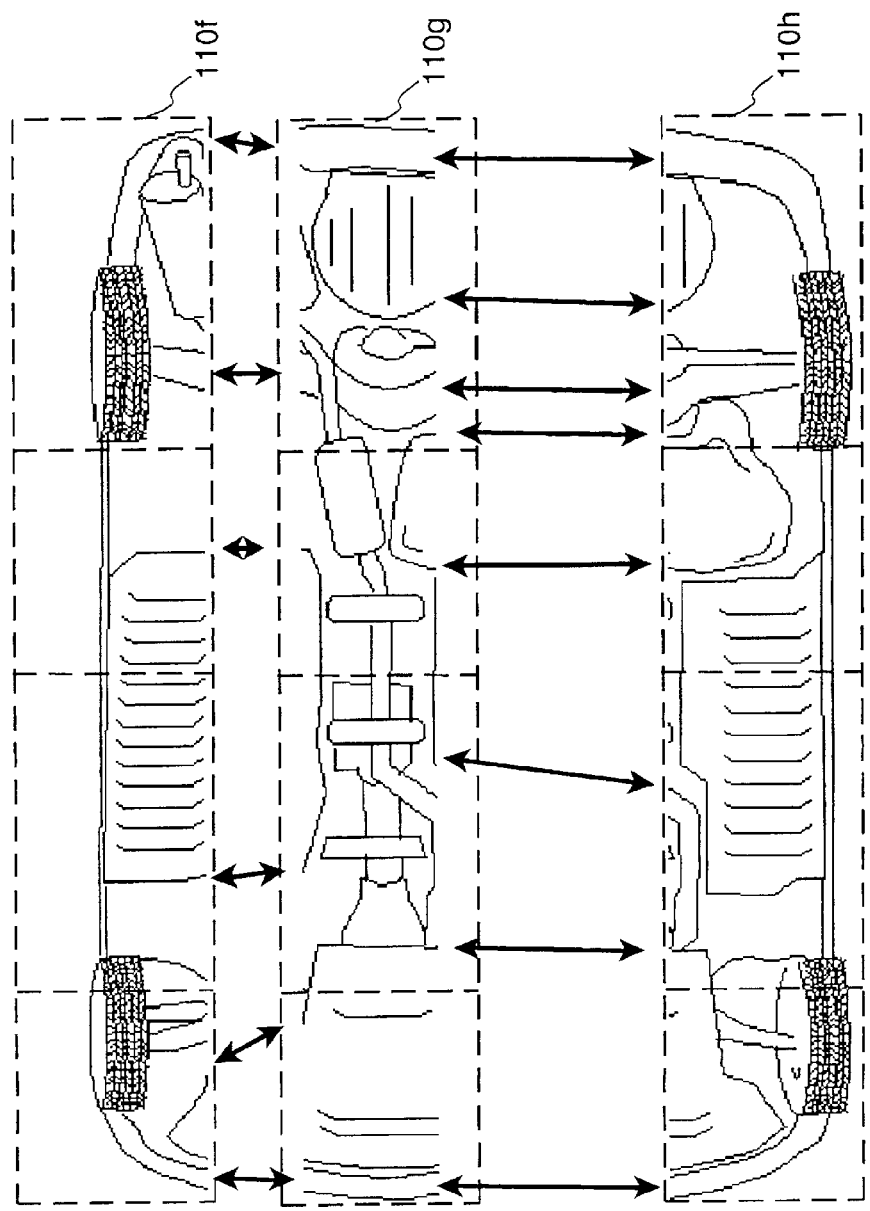
FIG. 11 illustrates how multiple strip photos are combined to create a full image of the undercarriage of a vehicle.

Once a strip photo has been created for each group of images taken from each camera of the imaging bar, the strip photos (110f, 110g, 110h) can then be combined by finding common features in the regions of the strips adjacent each other, as shown in FIG. 11, resulting from the FOV overlap of adjacent cameras.

Figure 12:
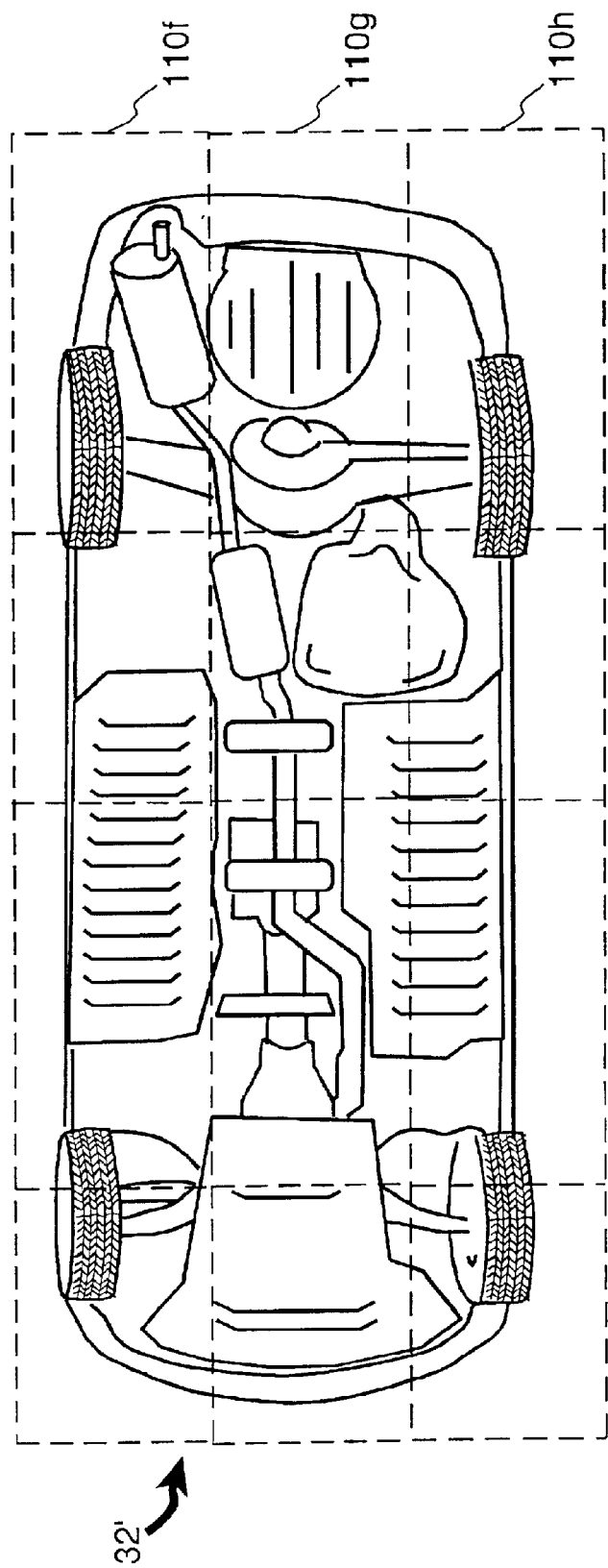
FIG. 12 depicts the generated full view image of the vehicle undercarriage.

Finally, when the strip photos have been stitch to each other, a composite image of the vehicle underside (32') is rendered as shown in FIG. 12. This image can then be displayed to an inspector or operator for analysis, in the most fundamental realization of the invention. The display of the rendered composite image may be made on a video monitor, computer display or three-dimensional headset, as previously described. As such, the basic embodiment of the invention may include the imaging bar, a computing platform with display, and image processing software has previously discussed.

Figure 15:
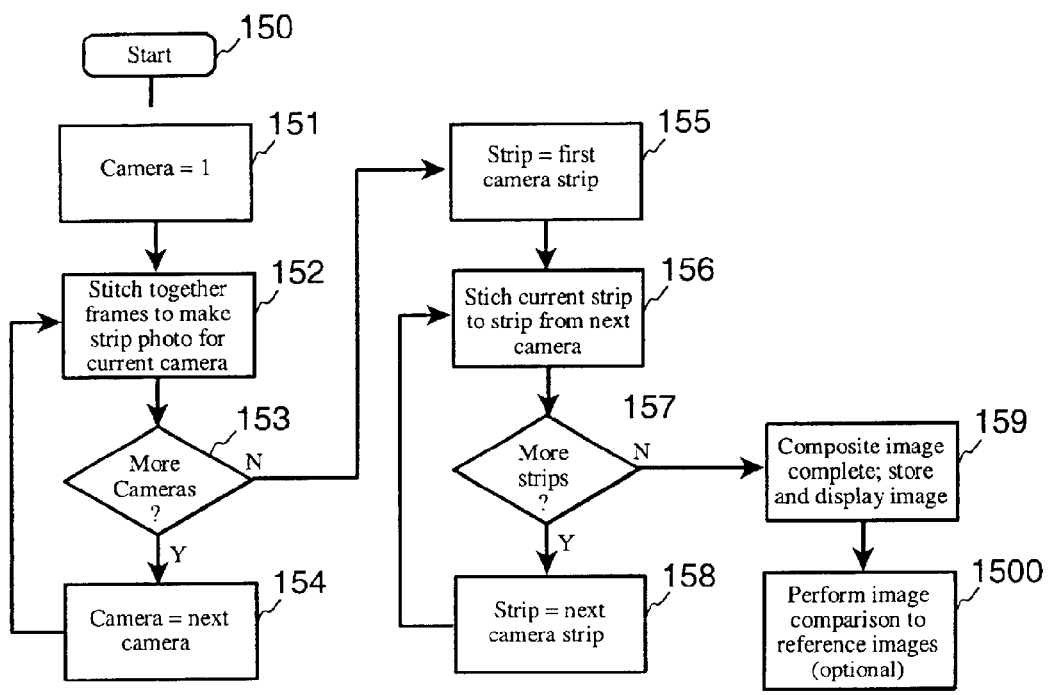
FIG. 15 shows the logical process according to the invention of rendering a composite image from the image frames.

FIG. 15 graphically depicts this logical process, first by stitching together a strip of photos from each camera (151, 152, 153, 154), followed by stitching strips (155, 156, 157, and 158) into a single composite image, and displaying the composite image (159), optionally followed by image comparison to reference images (1500) according to the enhanced embodiments.

These figures have illustrated only a few frames and strips for ease of understanding, while in practice, many more cameras are placed along the length of the imaging bar, and many more image sets are taken along the length of the vehicle, resulting in more steps of stitching frames into strips and strips into a single composite image.

Image Overlap Generation

Figure 17:
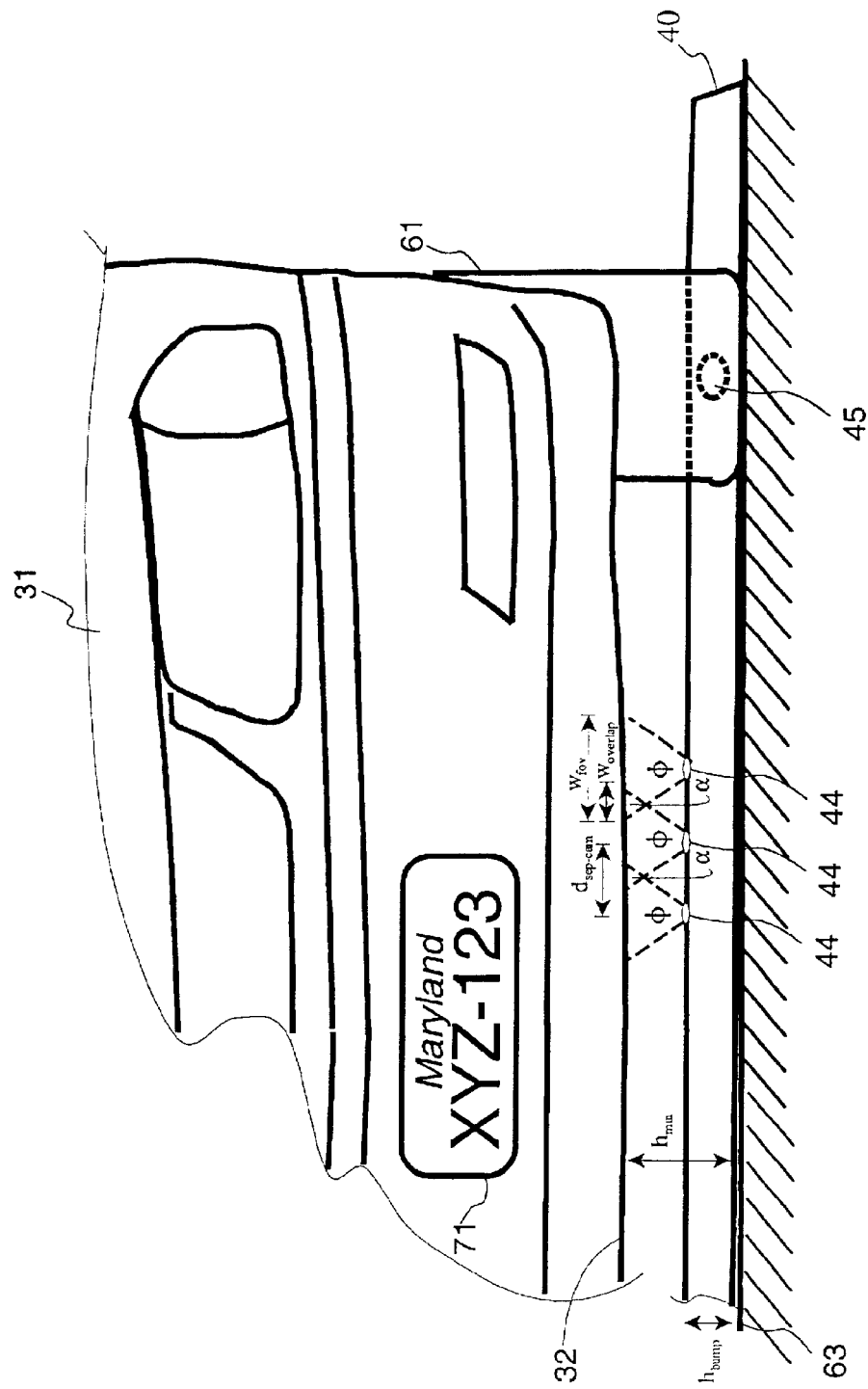
FIG. 17 illustrates the geometrical dimensions for establishing the maximum camera-to-camera spacing to achieve desired image edge overlap between sequential or adjacent images.

Referring now to FIG. 17, and having presented the fundamental image processing method and range finding/position determination method of the invention, we can now discuss in more detail:

(a) the mechanical design criteria for the spacing of the cameras for the generation of overlapping images in a first axis (side-to-side); and (b) the image capture timing process for the generation of overlapping images in a second axis (lengthwise).

In FIG. 17, details of how the ideal camera-to-camera spacing is determined based upon the camera FOV, desired image overlap (side-to-side), and the minimum expected height of the vehicle undercarriage to be inspected and imaged.

In general, for any fixed spacing between cameras, the higher the vehicle chassis (over a minimum height), the greater the amount of imaging overlap between image frames taken from adjacent cameras (side-to-side images). As such, a "worst case" scenario involves defining a mimimum height or ground clearance of the vehicle $h_{min}$ to be inspected, selecting a camera with a given field of view $\phi$, and selecting a desirable minimum width of image overlap $w_{fov}$. As such, a formula for determining the maximum spacing between adjacent cameras can be expressed as:

$$d_{sep\text{-}cam\text{-}max} = w_{fov} - w_{overlap\text{-}min} = [2 \cdot (h_{min} - h_{bump}) \cdot \tan(\tfrac{1}{2}\phi)] - w_{overlap\text{-}min}$$

where $d_{sep\text{-}cam\text{-}max}$ is the maximum camera-to-camera aperture (44) spacing to achieve the desired image overlap;

$w_{fov}$ is the width of the field of view of the selected camera at the maximum vehicle clearance height;

$w_{overlap-min}$ is the minimum image overlap to facilitate successful image panel matching and stitching together;

$h_{min}$ is the minimum height or ground clearance of a vehicle to be imaged;

$h_{bump}$ is the height of the aperture (44) from the ground (e.g. height of the "speed bump" housing); and φ is the angle of field of view of the selected camera.

Using this formula, and selecting a minimum vehicle clearance of 6 inches, a minimum overlap of images of 1 inch, a camera such as the Pelikan CCM630 ultra miniature color camera which has a FOV angle of 78°, and a speed bump height of 2 inches, the maximum spacing between cameras can be calculated as:

$$d_{sep-cam-max} = \left[2 \cdot (6-2) \cdot \tan\left(\frac{1}{2} \cdot 78\right)\right] - 1$$

$$\approx [8 \cdot 0.81] - 1$$

$$\approx 5.5 \text{ inches(approximately)}$$

So, for an imaging bar of approximately 80 inches in width (sufficient to image most automobiles), a preferred embodiment would include 14 or 15 cameras spaced approximately 5.5 inches apart. Selecting cameras with wider fields of view can reduce the number of cameras needed, which reduces maximum camera-to-camera spacing, assuming the minimum vehicle clearance is held constant. Likewise, increasing the minimum vehicle height may allow the camera spacing to be increased, also decreasing the number of cameras required in the assembly. Alternatively, selecting cameras with wider fields of view may allow vehicles with lower ground clearance to be imaged, assuming the camera-to-camera spacing is held constant.

As such, the particular dimensions, assumptions and selections of the foregoing example are for illustrative purposes only, and it will be recognized by those skilled in the art that many variations to these factors may be made without departing from the spirit and scope of the invention.

Figure 18:
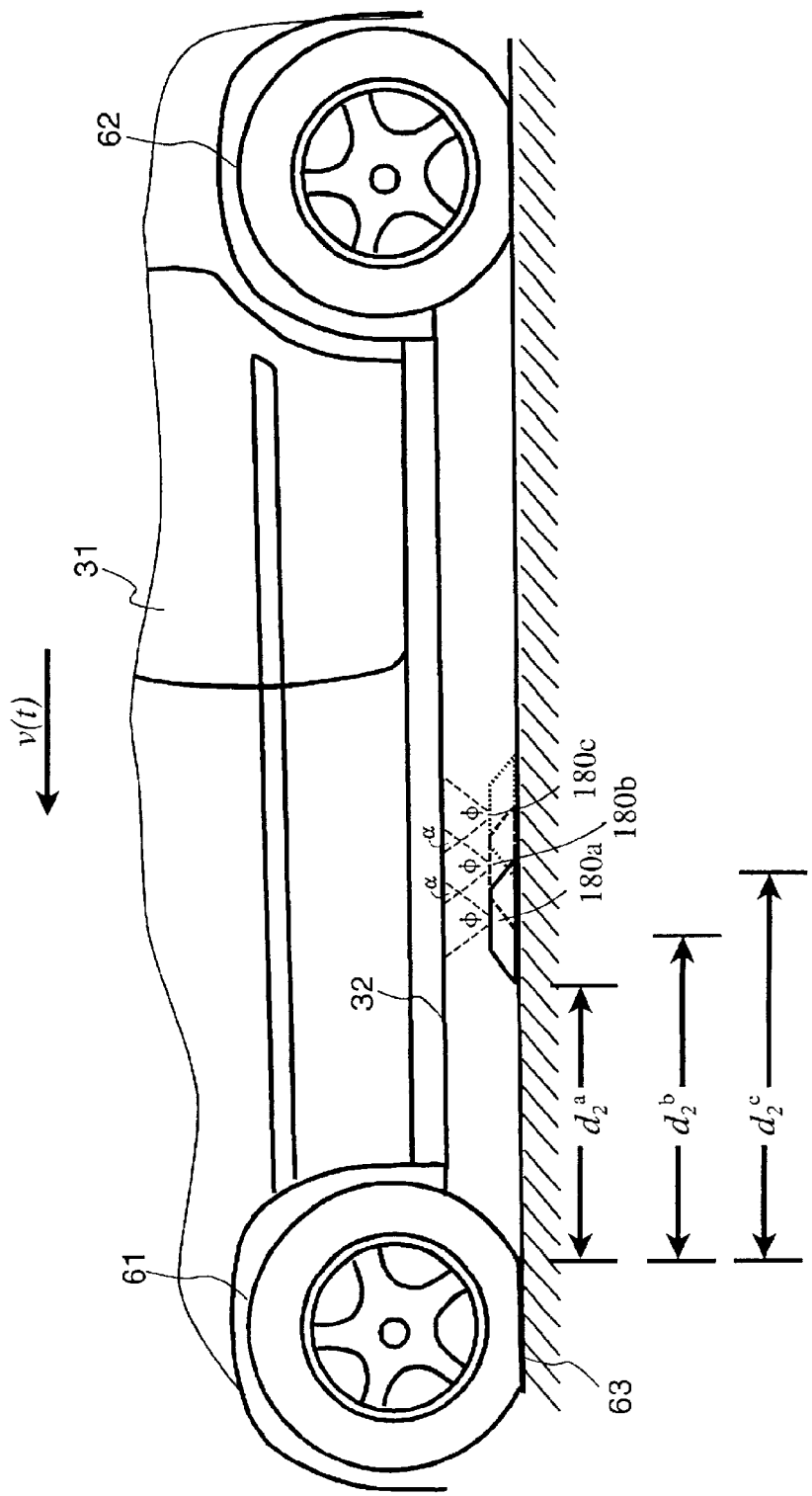
FIG. 18 depicts the sequential image capturing process to obtain image frames in a lengthwise manner along the vehicle in order to generate the desired image overlap.

Now, we turn our attention to FIG. 18, in which three successive positions (180a, 180b, 180c) of the vehicle over the imaging bar are shown as a vehicle passes over it with a time-varying velocity v(t). This particular view is of the phase when the imaging bar is between the front wheels (61) and the rear wheels (62). The following process, however, may be used while the imaging bar is in front of the front wheels (61) or behind the rear wheels (62), as well.

The goal of the image capture timing process is to capture images from each camera at a moment which will generate an overlap α in the image with the previous image taken from the same camera. This will generate a "lengthwise" overlap between frames taken successively from the same camera, to be used during the process of generating the composite "strip" images from each camera. In this axis, though, the overlap α is not determined by the side-to-side camera spacing, but is determined by the speed of the vehicle v(t) passing over the imaging bar and the timing of the coapturing of the image frames.

As the driver may increase and decrease his or her speed at will while passing over the imaging bar, the method of the invention compensates for these variations in speed by repetitively measuring the distance from the imaging bar to one of the wheels, such as the distance to the front wheel $d_2$ (as shown in FIG. 6 initially), using the range finding devices. Therein lies one of the substantial advantages of the present invention over the system of the prior art. Wherein the system of the prior art uses two induction loops, one just ahead of the imaging slit and one just after the slit, it must assume a relatively constant speed of travel of the vehicle over the imaging slit. While this may be a reasonable premise for below-grade systems which are installed below and level with the surface of the roadway; this, however, is not a reasonable assumption for an above-grade system because a driver will naturally slow the vehicle speed as the wheels encounter the above-grade housing of an imaging system, and will accelerate slightly when the wheels are clear of the above-grade housing. Thus, one important aspect of providing a portable, above-grade undercarriage imaging system is to provide compensation within the imaging system for the time-varying speed of the vehicle, as our invention does.

As such, as a suitable distance from the wheel is achieved to take the next image frame from each camera ($d_2^a$, $d_2^b$, $d_2^c$, . . . ), a sequential image is captured from each camera for later assembly into the lengthwise strip images. Because many cameras have an essentially square imaging field, and because the physical dimensions of this situation match the dimension of the calculation for camera-to-camera spacing (e.g. vehicle minimum clearance, imaging bar height, etc.), in many system configurations, the same value as determined for the camera-to-camera spacing may be used as the increment value for capturing images at different bar-to-wheel distances ($d_2^a$, $d_2^b$, $d_2^c$, . . . ) to achieve a similar lengthwise overlap α. So, in the previous example, images may be captured when:

$d_2^b = d_2^a + 5.5$ inches;

$d_2^c = d_2^b + 5.5$ inches; and so on.

Or, expressed more generally:

$d_n^{i+1} = d_n^i + d_{sep-cam-max}$ where:

$d_n^{i+1}$ is the distance at which the next (i+1) successive image is taken from a particular camera based upon the instantaneous distance ($d_n = d_1$, $d_2$, $d_3$ or $d_4$ depending on phase of imaging) between the imaging bar and the vehicle wheel;

$d_n^i$ is distance at which the previous or current image number was taken from a particular camera based upon the instantaneous distance ($d_n = d_1$, $d_2$, $d_3$ or $d_4$ depending on phase of imaging) between the imaging bar and the vehicle wheel; and $d_{sep-cam-max}$ is camera-to-camera spacing based upon the camera's field of view, minimum height of the vehicle to be imaged, height of the imaging bar, and desired image overlap, and assuming an relatively square imaging field.

The ultrasonic range finder model M5000/95 from Massa Products Corporation of the preferred embodiment provides for a minimum range of 1 foot (12 inches), a maximum range of 13 feet, with an accuracy of approximately 0.4 inches. A unit such as this provides the accuracy needed to support the example desired overlap. To accommodate the minimum range characteristic of this particular unit, as a wheel moves within the minimum range of a front or forward range finder, the method may switch to using the measurement from the opposite range finder set which should "see" a distance to the other vehicle wheels (front or forward) greater than the minimum range finding distance. Alternate range finder units may be employed which may not exhibit this minimum range characteristic, or a combination of short-range and long-range finders may be employed, as well.

So, for a vehicle having a body length of 110 inches, approximately 20 images from each camera would be captured (lengthwise). Multiplying this by the total of 15 cameras across the imaging bar of this example, a total of 300 to 320 image frames would be captured to fully image a typical automobile.

Of course, if the imaging field is not relatively square, such as a camera having a 3:1 or 4:1 aspect ratio, one may first determine which axis in which the widest imaging dimension will be placed (e.g. side-to-side or lengthwise), and then an appropriate adjustment to either the camera-to-camera spacing or the successive timed images may be made, but not both. It would be particularly advantageous with such a camera to align the longest dimension of the imaging frame with the side-to-side axis, such that fewer cameras could be employed in the imaging bar (e.g. greater camera-to-camera spacing), thereby reducing the cost of the assembly, number of images per bar position to be captured, etc. In such a non-square realization of the invention, the direct use of $d_{sep\text{-}cam\text{-}max}$ without adjustment in the image capture timing process may be possible, but may result in a smaller or larger overlap in one axis than in another axis. Therefore, the preferred embodiment allows for an adjustment of $d_{sep\text{-}cam\text{-}max}$ in one axis or another to maintain a similar overlap in both axes. As the timing of the capture of the images from cameras is preferably controlled by software running on the computing platform, the adjustment to the lengthwise overlap generation method is more readily achieved than the adjustment to the camera-to-camera spacing which is set by plastic molding dimensions.

Image Analysis and Comparison Process

In a more advanced embodiment of the invention, the rendered composite image may be compared to one or more reference images in order to enhance the ability of the operator to detect anomalies in the undercarriage structure.

Figure 13:
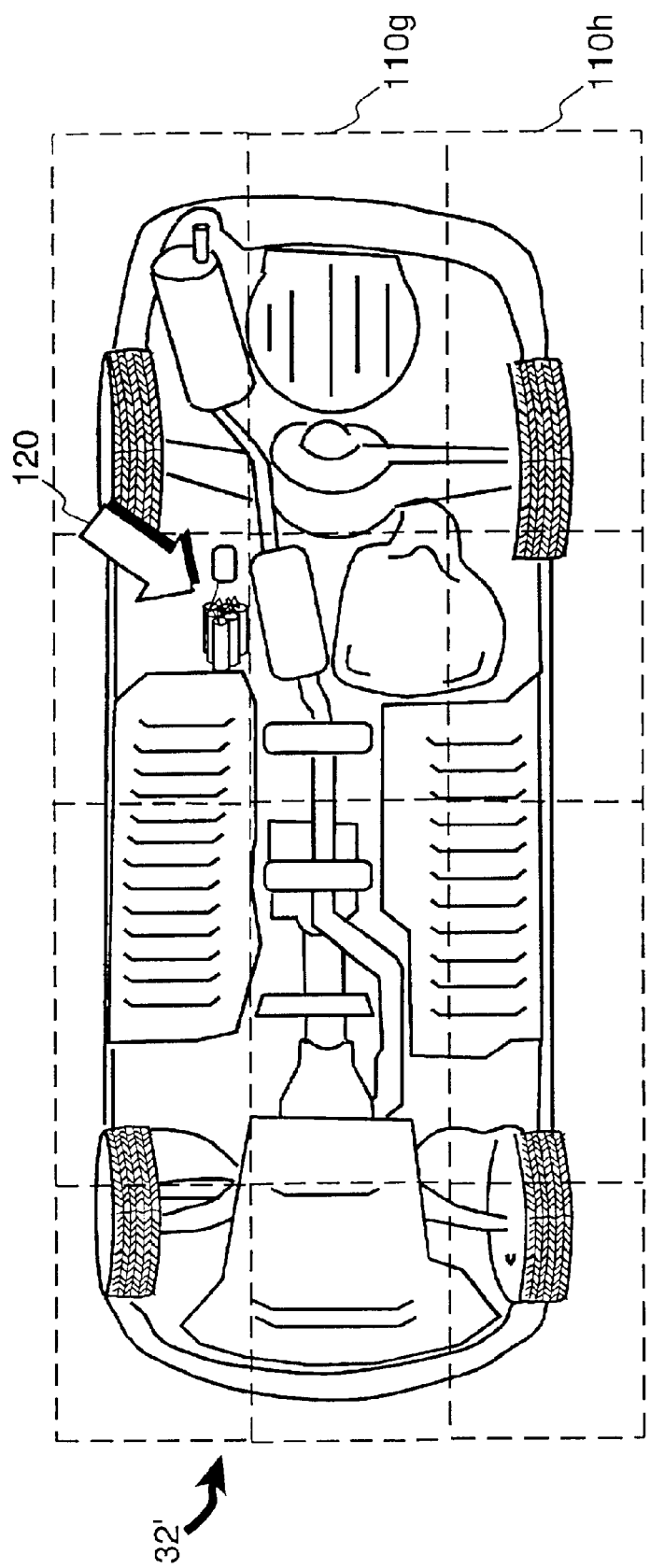
FIG. 13 provides an example user interface to alert the user of a detected variation between the image of the vehicle and a reference image.

First, the wheelbase can be used, possibly in conjunction with operator-supplied make and model criteria, to retrieve from a local database an image of the undercarriage of the same make and model vehicle as it was produced straight from the manufacturing line. Many times the vehicle identifier number ("VIN") which is visible through the lower portion of the windshield may be parsed to determine a make and model, as well. This image can also be retrieved via a computer network from a remote database server (82), as shown in FIG. 8. In the most basic form of comparison, the two images may be overlaid one upon another, possibly in different color schemes, wherein the user may visually scan for differences between the images. Any difference that is found may be manually inspected further with the hand mirror device of the prior art. In a more sophisticated analysis, the software may find the feature differences and highlight them on the display, such as by changing the color of the areas of difference, flashing the areas of difference, or placing a cursor or pointer (120) near the areas of difference, as shown in FIG. 13.

In another enhancement of the analysis process of the invention, the operator may enter a vehicle identifier criteria, such as a license plate number or VIN, to allow a previously stored image of that very vehicle to be retrieved and used as the reference image. If no previous image is available, the current image may be stored for future reference use. This approach may allow for detection of changes in the undercarriage structure of specific vehicles, for even greater detection capabilities.

Remote Image Storage, Retrieval and Sharing

As discussed in the previous paragraphs, composite images, make-and-model reference images, and previously stored vehicle-specific images may be stored locally at the computing platform, or they may be stored remotely at a remote database server. Remote storage provides several key advantages, including:

(1) allows the images to be used at multiple inspection stations on the network, thereby increasing the possibility of detection of undercarriage anomalies;

(2) allows make-and-model images to be maintained and updated in a centralized location; and (3) reduces the storage requirements for the local computing platforms.

Figure 16:
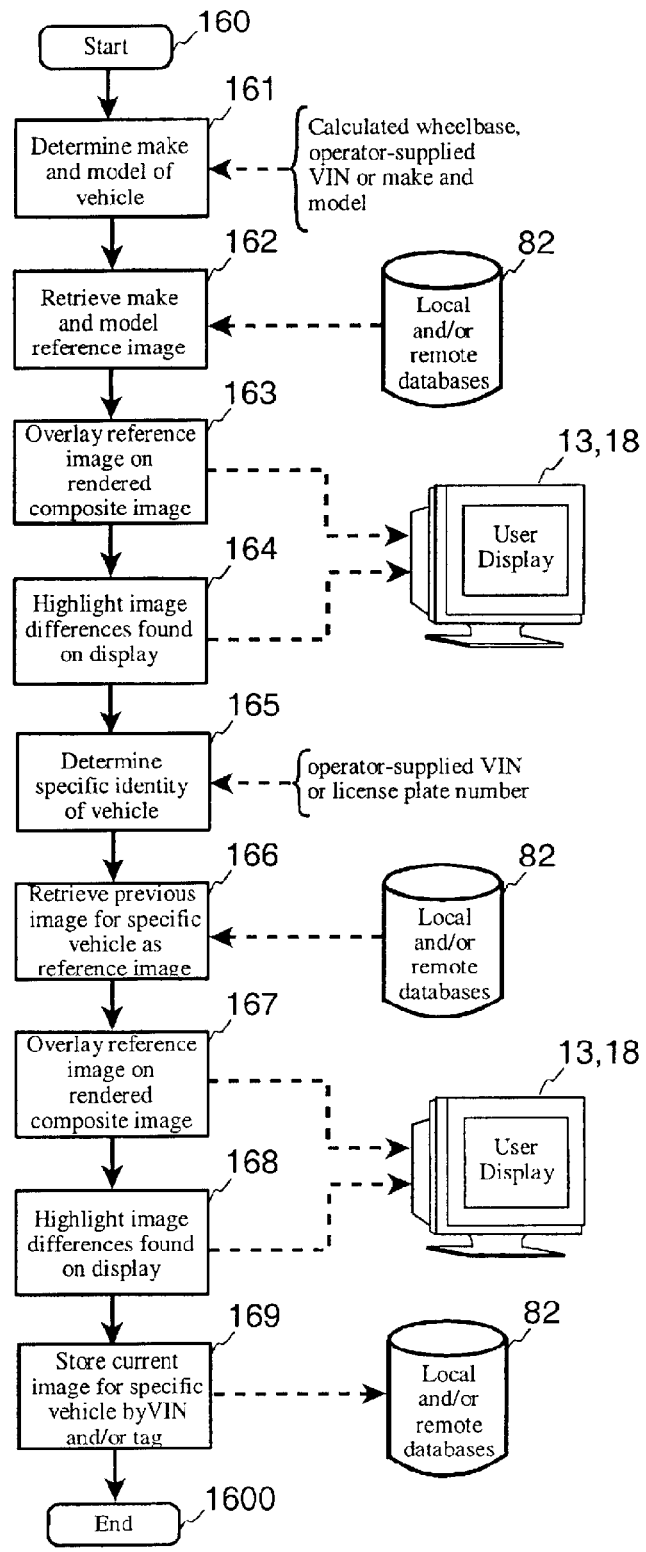
FIG. 16 shows the logical process of retrieving reference images and overlaying them onto the rendered composite image for comparison and analysis

Turning to FIG. 16, the entirety of the process display and analysis according to the preferred embodiment, with the previously described steps, is shown. Initially, the make and model of the vehicle is determined (161) from the wheelbase measurement (made with the range finders), and operator-supplied VIN or make-and-model indicators. Next, if a reference image for that make and model of vehicle is available in a local or remote database (82), the reference image is retrieved (162) and overlaid on the rendered composite image (163) for display to the user. If automatic feature difference comparison is implemented, the differences may be highlighted (164) on the display, too.

Then, using the operator-supplied VIN or license plate number (165), if a previously captured image of the specific vehicle's undercarriage is available locally or remotely (82), that image is retrieved (166) and overlaid on the rendered composite image (167) for display to the user, including automatically detected difference highlights (168), if implemented.

Finally, the rendered composite image may be stored (169) locally and/or remotely for future referenced, keyed by license plate number and/or VIN.

Remote Expertise Access

In a more advanced realization of the invention, a remote center of experts (83) may be consulted for further analysis. In such a case, the rendered composite image, retrieved make-and-model and vehicle-specific reference images, along with any comparison images (overlaid images) may be transmitted by the computing platform (80) to a similar computing platform at the remote analysis center (83) via a computer network (e.g. wireless LAN, Internet, secure network, etc.). There, specific experts may be consulted, such as trained technicians for the make and model of that vehicle, as well as experts at drug and contraband interdiction or demolitions and explosives experts.

Stereoscopic Viewing

As previously disclosed, in a typical configuration with a typical camera, the camera-to-camera spacing may be a maximum of 5.5 inches along the imaging bar, with a similar lengthwise "snapshotting" method every 5.5 inches. Decreasing these values, however, increases the amount of overlap generated in adjacent and sequential image frames, and increases the number of images to be stitched together to render a composite, single view of the entire undercarriage.

If the camera-to-camera spacing and the lengthwise snapshotting is decreased by approximately one-half of this value, or to 2.25 inches, simulated stereoscopic viewing may be provided by the system. As the human eyes are located approximately 2.25 to 2.5 inches apart, this camera spacing accurately simulates a human view point from the same point of the camera apertures. As such, the system may display two image frames, either adjacent side-to-side camera images or sequential same-camera lengthwise images, in the left and right displays of the three-dimensional "virtual reality" viewing glasses (84) of the preferred embodiment.

With each eye viewing a different image taken from the appropriately spaced vantage points, the image of the undercarriage will appear to be three-dimensional, which can provide additional capabilities to detect anomalies under the vehicle.

Conclusion

While the foregoing disclosure of the invention has employed both generalized processes, systems, and components as well as specific illustrative examples, and while certain details of a preferred embodiment and multiple alternate and enhanced embodiments have be provided, it will be recognized by those skilled in the art that certain variations, substitutions, or alternations may be made without departing from the spirit and scope of the invention, including but not limited to use of alternate programming languages and methodologies, alternate computing platforms, and equivalent data structures and logical processes.

What is claimed is:

1. A method for rendering a viewable image of a vehicle undercarriage comprising the steps of:
   arranging a plurality of imaging devices with a first dimensional spacing between said imaging device such that a first area of overlap within adjacent imaging device fields of view is provided;
   measuring a range from said imaging devices to a vehicle while a vehicle passes over said plurality of imaging devices;
   storing a plurality of images from each imaging device by determining positions at which images from said imaging devices is stored with subsequent images from each imaging device having a second area of overlap within said imaging device field of views; and
   assembling a viewable undercarriage image of said overpassing vehicle by matching features in said stored images.

2. The method as set forth in claim 1 wherein said step of arranging a plurality of imaging devices comprises arranging a plurality of cameras in a row across a lane of vehicle traffic.

3. The method as set forth in claim 1 wherein said step of measuring a range from said imaging devices to a vehicle comprises making an ultrasonic measurement.

4. The method as set forth in claim 1 wherein said step of measuring a range from said imaging devices to a vehicle comprises making a laser range measurement.

5. The method as set forth in claim 1 wherein said step of assembling a viewable undercarriage image comprises assembling said subsequent images from each imaging device into a plurality of strip images, followed by assembling said strips into said a viewable undercarriage image.

6. The method as set forth in claim 1 wherein said step of assembling a viewable undercarriage image comprises assembling said images from adjacent imaging devices stored at each vehicle position into a plurality of strip images, followed by assembling said strips into said a viewable undercarriage image.

7. A computer readable medium encoded with software for rendering a viewable image of a vehicle undercarriage, said software when executed causing a computing platform to perform the steps of:
   arranging a plurality of imaging devices with a first dimensional spacing between said imaging device such that a first area of overlap within adjacent imaging device fields of view is provided;
   measuring a range from said imaging devices to a vehicle while a vehicle passes over said plurality of imaging devices;
   storing a plurality of images from each imaging device by determining positions at which images from said imaging devices is stored with subsequent images from each imaging device having a second area of overlap within said imaging device field of views; and
   assembling a viewable undercarriage image of said overpassing vehicle by matching features in said stored images.

8. The computer readable medium as set forth in claim 7 wherein said software for measuring a range from said imaging devices to a vehicle comprises software for making an ultrasonic measurement.

9. The computer readable medium as set forth in claim 7 wherein said software for measuring a range from said imaging devices to a vehicle comprises software for making a laser range measurement.

10. The computer readable medium as set forth in claim 7 wherein said software for assembling a viewable undercarriage image comprises software for assembling said subsequent images from each imaging device into a plurality of strip images, followed by assembling said strips into said a viewable undercarriage image.

11. The computer readable medium as set forth in claim 7 wherein said software for assembling a viewable undercarriage image comprises software for assembling said images from adjacent imaging devices stored at each vehicle position into a plurality of strip images, followed by assembling said strips into said a viewable undercarriage image.

12. A system for imaging a vehicle undercarriage comprising:
   a plurality of imaging devices in an array with inter-device spacing which provides a first area of overlap in fields of view of adjacent imaging devices at a minimum clearance distance from an arrangement, each of said imaging devices having an image output;
   at least one range finding device positioned relative to said imaging device array in a manner capable of measuring a distance to a vehicle passing over said imaging device array, said range finding device having a range measurement output;
   one or more communications means disposed between said range finding device output and an image rendering device range measurement input, and between said imaging device image output and an image storing device image collection input;
   an image storing device having said image collection input and said range measurement input, said image storing device being adapted to determine positions of said vehicle at which subsequent images from each imaging device may be stored, said subsequent images having a second area of overlap; and
   an image rendering device adapted to assemble a viewable image of an undercarriage of said overpassing vehicle by matching features in said stored images.

13. The system as set forth in claim 12 wherein said array of imaging devices comprises an array of cameras disposed in a housing which resembles a traffic speed bump.

14. The system as set forth in claim 12 wherein said range finding device comprises an ultrasonic range finder.

15. The system as set forth in claim 12 wherein said range finding device comprises a laser range finder.

16. The system as set forth in claim 12 wherein said range finding device comprises a range finder positioned in a manner relative to said array of imaging devices such that a distance from said overpassing vehicle's wheels to said array may be measured.

17. The system as set forth in claim 12 wherein said communications means comprises a computer bus.

18. The system as set forth in claim 12 wherein said image storing device comprises a computer readable medium associated with a image capturing controller.

19. The system as set forth in claim 12 wherein said image rendering device comprises a computer readable medium associated with a image processing means.

* * * * *

UNITED STATES PATENT AND TRADEMARK OFFICE
CERTIFICATE OF CORRECTION

PATENT NO. : 6,856,344 B2
DATED : February 15, 2005
INVENTOR(S) : Robert H. Frantz It is certified that error appears in the above-identified patent and that said Letters Patent is hereby corrected as shown below:

Title page,
Item [12], change "Franz" to -- Frantz --
Item [75], Inventor, change "Franz" to -- Frantz --.

Signed and Sealed this

Seventeenth Day of May, 2005

JON W. DUDAS
*Director of the United States Patent and Trademark Office*